(12) United States Patent
Takahashi et al.

(10) Patent No.: US 11,883,120 B2
(45) Date of Patent: Jan. 30, 2024

(54) MEDICAL OBSERVATION SYSTEM, MEDICAL SIGNAL PROCESSING DEVICE, AND MEDICAL SIGNAL PROCESSING DEVICE DRIVING METHOD

(71) Applicant: SONY CORPORATION, Tokyo (JP)

(72) Inventors: Yasuaki Takahashi, Kanagawa (JP);
Kenji Takahashi, Kanagawa (JP);
Hisakazu Shiraki, Kanagawa (JP);
Masahito Yamane, Kanagawa (JP);
Masaya Takemoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 779 days.

(21) Appl. No.: 16/770,257

(22) PCT Filed: Nov. 8, 2018

(86) PCT No.: PCT/JP2018/041443
§ 371 (c)(1),
(2) Date: Jun. 5, 2020

(87) PCT Pub. No.: WO2019/123874
PCT Pub. Date: Jun. 27, 2019

(65) Prior Publication Data
US 2021/0369080 A1    Dec. 2, 2021

(30) Foreign Application Priority Data

Dec. 18, 2017 (JP) .................................. 2017-242041
Dec. 18, 2017 (JP) .................................. 2017-242042

(51) Int. Cl.
*A61B 1/00* (2006.01)
*A61B 34/00* (2016.01)
(Continued)

(52) U.S. Cl.
CPC ............ *A61B 34/35* (2016.02); *A61B 1/0005* (2013.01); *A61B 1/00006* (2013.01);
(Continued)

(58) Field of Classification Search
CPC . A61B 1/000095; A61B 1/0005; A61B 34/25; A61B 34/37; A61B 90/361;
(Continued)

(56) References Cited

U.S. PATENT DOCUMENTS

2003/0004397 A1    1/2003  Kameya et al.
2003/0093503 A1    5/2003  Yamaki et al.
(Continued)

FOREIGN PATENT DOCUMENTS

JP    2003-010112 A    1/2003
JP    2003-265501 A    9/2003
(Continued)

OTHER PUBLICATIONS

"Stereoscopic Visualization and 3-D Technologies in Medical Endoscopic Teleoperation"—Salvatore Livatino et al., IEEE Transactions on Industrial Electronics, vol. 62, No. 1, Jan. 2015 (Year: 2015).*
International Search Report and Written Opinion of PCT Application No. PCT/JP2018/041443, dated Jan. 29, 2019, 12 pages of ISRWO.

*Primary Examiner* — Mainul Hasan
(74) *Attorney, Agent, or Firm* — CHIP LAW GRUOP

(57) ABSTRACT

Provided is a medical observation system that includes a first medical signal processing device including a first signal processing unit that acquires first image data corresponding to a result of image capturing of an affected part by a medical observation device and provides first signal processing to the first image data, and a second medical signal processing device including a second signal processing unit that acquires second image data corresponding to the result of image capturing from the first medical signal processing device through a predetermined network and provides sec-
(Continued)

ond signal processing to the second image data. The second signal processing unit transmits information related to the second signal processing to the first medical signal processing device. The first signal processing unit controls the first signal processing based on the second signal processing.

31 Claims, 11 Drawing Sheets

(51) Int. Cl.
  *A61B 34/37* (2016.01)
  *A61B 90/20* (2016.01)
  *A61B 90/00* (2016.01)
  *A61B 34/35* (2016.01)
  *A61B 34/30* (2016.01)

(52) U.S. Cl.
  CPC ...... *A61B 1/0019* (2013.01); *A61B 1/000095* (2022.02); *A61B 34/25* (2016.02); *A61B 34/37* (2016.02); *A61B 90/20* (2016.02); *A61B 90/361* (2016.02); *A61B 90/37* (2016.02); *A61B 2034/302* (2016.02)

(58) Field of Classification Search
  CPC ..... A61B 90/37; A61B 1/00006; A61B 34/35; A61B 34/30
  See application file for complete search history.

(56) References Cited

U.S. PATENT DOCUMENTS

| | | | |
|---|---|---|---|
| 2004/0225185 A1* | 11/2004 | Obata | A61B 1/042 600/118 |
| 2004/0230094 A1* | 11/2004 | Nakamura | A61B 1/00183 600/101 |
| 2007/0173689 A1* | 7/2007 | Ozaki | A61B 1/0004 600/118 |
| 2008/0294000 A1* | 11/2008 | Iwamoto | A61B 1/0005 600/103 |
| 2014/0176533 A1* | 6/2014 | Dillavou | G06T 19/006 345/419 |
| 2018/0042454 A1* | 2/2018 | Iwasaki | A61B 1/00006 |
| 2018/0064505 A1* | 3/2018 | Zhao | G16H 40/63 |
| 2018/0250086 A1* | 9/2018 | Grubbs | A61B 34/35 |
| 2019/0090969 A1* | 3/2019 | Jarc | A61B 34/25 |

FOREIGN PATENT DOCUMENTS

| | | |
|---|---|---|
| JP | 2004-077828 A | 3/2004 |
| JP | 2004-180857 A | 7/2004 |
| JP | 2005-118232 A | 5/2005 |
| JP | 2008-253586 A | 10/2008 |
| JP | 2009-069855 A | 4/2009 |
| JP | 2009-279181 A | 12/2009 |
| JP | 2012-073940 A | 4/2012 |

* cited by examiner

ND SIGNAL PROCESSING
MEDICAL OBSERVATION SYSTEM, MEDICAL SIGNAL PROCESSING DEVICE, AND MEDICAL SIGNAL PROCESSING DEVICE DRIVING METHOD

CROSS REFERENCE TO RELATED APPLICATIONS

This application is a U.S. National Phase of International Patent Application No. PCT/JP2018/041443 filed on Nov. 8, 2018, which claims priority benefit of Japanese Patent Application No. JP 2017-242042 filed in the Japan Patent Office on Dec. 18, 2017 and claims priority benefit of Japanese Patent Application No. JP 2017-242041 filed in the Japan Patent Office on Dec. 18, 2017. Each of the above-referenced applications is hereby incorporated herein by reference in its entirety.

FIELD

The present disclosure relates to a medical observation system, a medical signal processing device, and a medical signal processing device driving method.

BACKGROUND

Recently, surgery (what is called micro surgery) in which various treatments are provided while an affected part is observed by using a medical observation device such as a surgical microscope or an endoscope is being frequently performed due to development of surgical methods and surgical instruments. Such medical observation devices include not only a device that allows optical observation of an affected part but also a disclosed device configured to cause a display device such as a monitor to display, as an electronic image, an image of the affected part captured by an image capturing device (camera) or the like. For example, Patent Literature 1 discloses an example of what is called an electronic endoscope system that causes a display unit to display an endoscope image captured by an endoscope and allows observation and treatment to be performed while the image is viewed.

CITATION LIST

Patent Literature

Patent Literature 1: JP 2005-118232 A

SUMMARY

Technical Problem

At a medical site, it is assumed that an aged surgeon is retired from surgery due to physical problem. However, a junior surgeon often takes time to become independent because surgery experience is needed. With such a background, it is assumed that the number of surgeons is insufficient and a junior surgeon performs surgery while being instructed by an experienced aged surgeon.

However, it is sometimes difficult for an aged surgeon to attend surgery due to physical problem. Thus, it has been required to introduce a technology that enables a doctor (for example, a junior surgeon) performing manipulation in a surgery room to be instructed by another doctor (for example, an aged surgeon) in a room different from the surgery room.

Thus, the present disclosure provides a technology with which a task cooperatively performed by a plurality of doctors spatially isolated from each other can be achieved in a more preferable aspect.

Solution to Problem

According to the present disclosure, a medical observation system is provided that includes: a first medical signal processing device including a first signal processing unit configured to acquire first image data corresponding to a result of image capturing of an affected part by a medical observation device and provide first signal processing to the first image data; and a second medical signal processing device including a second signal processing unit configured to acquire second image data corresponding to the result of image capturing from the first medical signal processing device through a predetermined network and provide second signal processing to the second image data, wherein the second signal processing unit transmits information related to the second signal processing to the first medical signal processing device, and the first signal processing unit controls the first signal processing in accordance with the second signal processing.

Moreover, according to the present disclosure, a medical signal processing device is provided that includes a signal processing unit configured to provide first signal processing to first image data corresponding to a result of image capturing of an affected part by a medical observation device, wherein the signal processing unit controls the first signal processing in accordance with second signal processing provided to second image data corresponding to the result of image capturing at another device.

Moreover, according to the present disclosure, a medical signal processing device is provided that includes a signal processing unit configured to acquire second image data corresponding to a result of image capturing of an affected part by a medical observation device from another device and provide second signal processing to the second image data, wherein the signal processing unit transmits information related to the second signal processing to the other device configured to control first signal processing on first image data corresponding to the result of image capturing.

Moreover, according to the present disclosure, a medical observation system is provided that includes: a medical observation device; and a medical signal processing device, wherein the medical signal processing device includes a first signal processing unit configured to provide signal processing to first image data corresponding to a result of image capturing of an affected part by the medical observation device to generate second image data, a first output control unit configured to control a first output unit to output an image corresponding to the second image data, and a forwarding processing unit configured to forward the first image data to another device.

Moreover, according to the present disclosure, a medical signal processing device is provided that includes: a signal processing unit configured to provide signal processing to first image data corresponding to a result of image capturing of an affected part by a medical observation device to generate second image data; an output control unit configured to control an output unit to output an image corresponding to the second image data; and a forwarding processing unit configured to forward the first image data to another device.

Moreover, according to the present disclosure, a medical signal processing device driving method is provided that includes, by a computer: providing signal processing to first image data corresponding to a result of image capturing of an affected part by a medical observation device to generate second image data; controlling an output unit to output an image corresponding to the second image data; and forwarding the first image data to another device.

Advantageous Effects of Invention

As described above, the present disclosure provides a technology with which a task cooperatively performed by a plurality of doctors spatially isolated from each other can be achieved in a more preferable aspect.

The above-described effect is not necessarily restrictive, but any effect indicated in the present specification or any other effect that could be understood from the present specification may be achieved together with or in place of the above-described effect.

DESCRIPTION OF EMBODIMENTS

Preferable embodiments of the present disclosure will be described below in detail with reference to the accompanying drawings. In the present specification and drawings, any components having functional configurations identical to each other in effect are denoted by an identical reference sign, and duplicate description thereof will be omitted.

The description is performed in an order below.
1. Exemplary configuration of medical observation system
2. Technical problem
3. Technological characteristics
   3.1. System configuration
   3.2. Functional configuration
   3.3. Examples
4. Exemplary hardware configuration
5. Exemplary application
6. Conclusion

1. EXEMPLARY CONFIGURATION OF MEDICAL OBSERVATION SYSTEM

Figure 1:
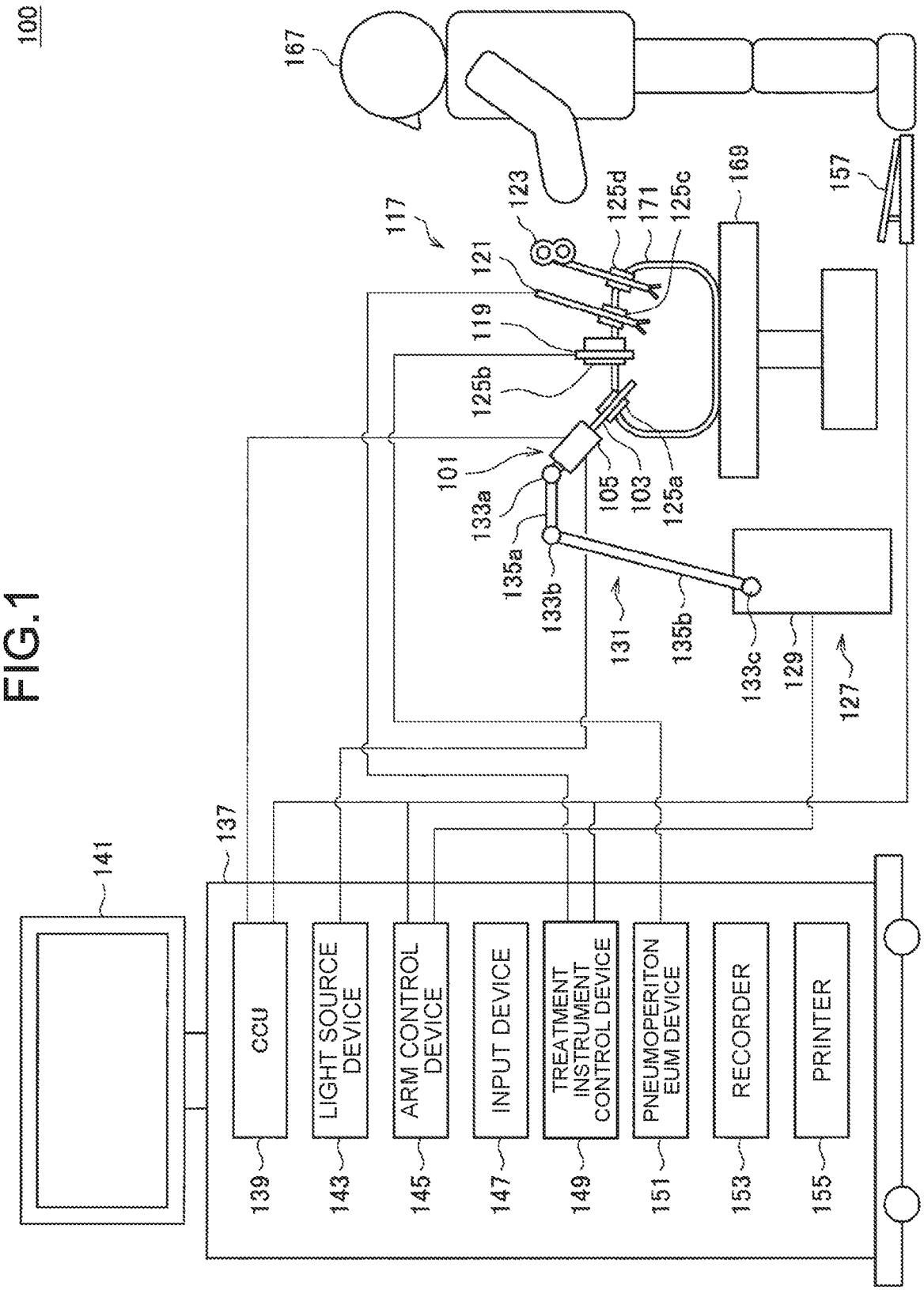
FIG. 1 is a diagram illustrating an exemplary schematic configuration of an endoscopic operation system to which the technology according to the present disclosure is applicable.
Figure 2:
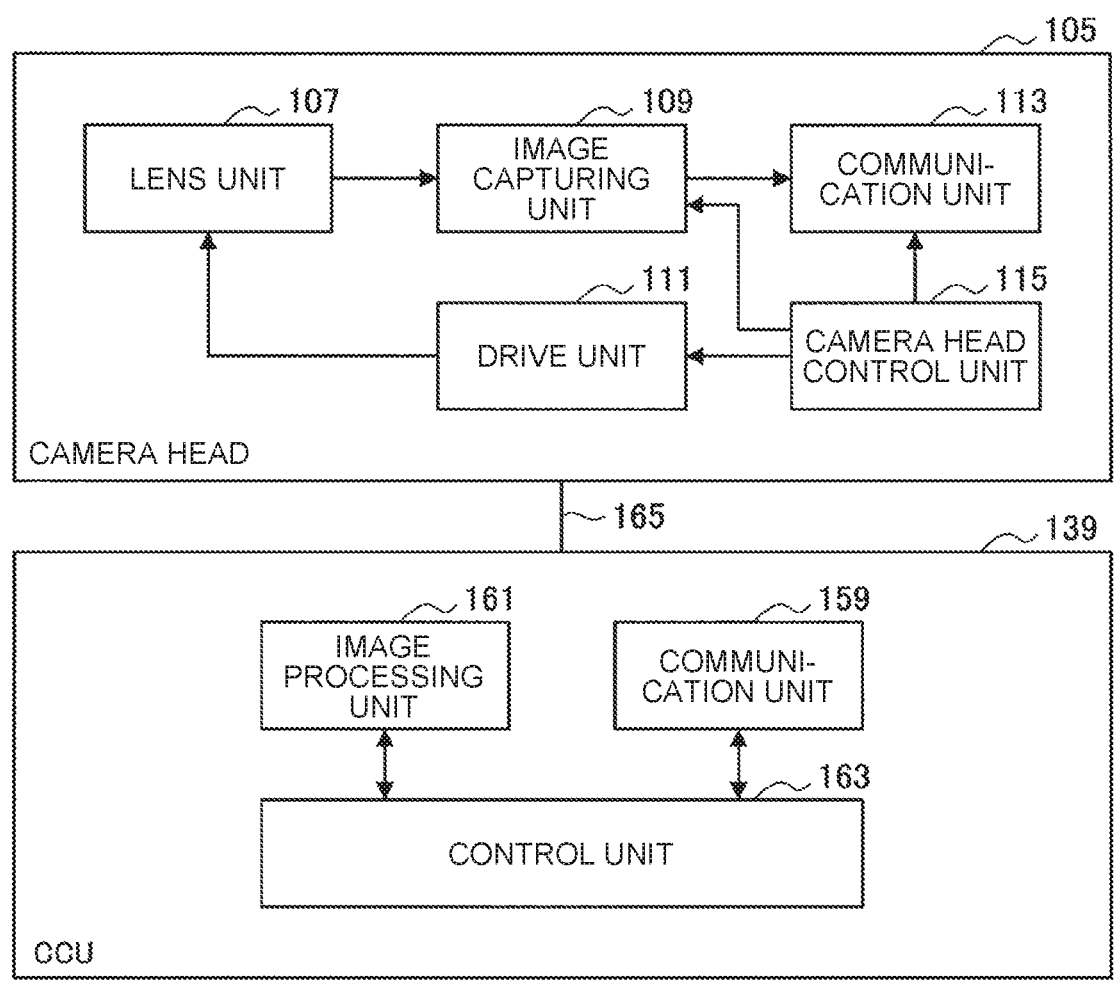
FIG. 2 is a block diagram illustrating exemplary functional configurations of a camera head and a CCU illustrated in FIG. 1.

The following first describes an example of what is called an endoscopic operation system as an exemplary schematic configuration of a medical observation system to which the technology according to an embodiment of the present disclosure is applicable with reference to FIGS. 1 and 2.

For example, FIG. 1 is a diagram illustrating an exemplary schematic configuration of an endoscopic operation system to which the technology according to the present disclosure is applicable. FIG. 1 illustrates a situation in which an operator (doctor) 167 performs surgery on a patient 171 on a patient bed 169 by using an endoscopic operation system 100. As illustrated in FIG. 1, the endoscopic operation system 100 includes an endoscope 101, other surgical instruments 117, a support arm device 127 supporting the endoscope 101, and a cart 137 on which various devices for an endoscopic operation are mounted.

In an endoscopic operation, the abdominal wall is punctured by a plurality of tubular puncture instruments called trocars 125a to 125d instead of being opened by cutting. Then, a lens barrel 103 of the endoscope 101 and the other surgical instruments 117 are inserted into the body cavity of the patient 171 through the trocars 125a to 125d. In the illustrated example, a pneumoperitoneum tube 119, an energy treatment instrument 121, and forceps 123 are inserted into the body cavity of the patient 171 as the other surgical instruments 117. The energy treatment instrument 121 performs tissue incision and peeling, blood vessel sealing, or the like by high frequency current and ultrasonic wave vibration. However, the illustrated surgical instruments 117 are merely exemplary, and the surgical instruments 117 may include various surgical instruments, such as a prick and a retractor, typically used in an endoscopic operation.

An image of a surgery site in the body cavity of the patient 171, which is captured by the endoscope 101 is displayed on a display device 141. The operator 167 performs treatment such as resection of an affected part by using the energy treatment instrument 121 and the forceps 123 while watching, in real time, the image of the surgery site displayed on the display device 141. Although not illustrated, the pneumoperitoneum tube 119, the energy treatment instrument 121, and the forceps 123 are supported by the operator 167, an assistant, or the like in surgery.

(Support Arm Device)

The support arm device 127 includes an arm unit 131 extending from a base unit 129. In the illustrated example, the arm unit 131 includes joint parts 133a, 133b, and 133c and links 135a and 135b, which are driven under control of an arm control device 145. The arm unit 131 supports the endoscope 101 and controls the position and posture thereof. Accordingly, the position of the endoscope 101 can be stably fixed.

(Endoscope)

The endoscope 101 includes the lens barrel 103, a region of which extending from a leading end by a predetermined length is inserted into the body cavity of the patient 171, and a camera head 105 connected with a base end of the lens barrel 103. In the illustrated example, the endoscope 101 is configured as what is called a rigid scope including the lens barrel 103 that is rigid, but the endoscope 101 may be configured as what is called a flexible scope including the lens barrel 103 that is flexible. The camera head 105 or the endoscope 101 including the camera head 105 corresponds to an exemplary "medical observation device".

An opening to which an objective lens is fitted is provided at the leading end of the lens barrel 103. The endoscope 101 is connected with a light source device 143, and light generated by the light source device 143 is guided to the leading end of the lens barrel through a light guide extended inside the lens barrel 103 and is emitted toward an observation target (in other words, an image capturing object) in the body cavity of the patient 171 through the objective lens. The endoscope 101 may be a direct-view scope, an oblique-view scope, or a side-view scope.

An optical system and an image sensor are provided inside the camera head 105, and reflected light (observation light) from the observation target is condensed onto the image sensor through the optical system. The image sensor photoelectrically converts the observation light, thereby generating an electric signal corresponding to the observation light, in other words, an image signal corresponding to an observation image. The image signal is transmitted to a camera control unit (CCU) 139 as RAW data. The camera head 105 has a function to adjust the magnification and the focal length by driving the optical system as appropriate.

The camera head 105 may be provided with a plurality of image sensors to achieve, for example, stereoscopic viewing (3D display). In this case, a plurality of relay optical systems are provided inside the lens barrel 103 to guide the observation light to the respective image sensors.

(Various Devices Mounted on Cart)

The CCU 139 includes a central processing unit (CPU) and a graphics processing unit (GPU) and collectively controls the operation of the endoscope 101 and the display device 141. Specifically, the CCU 139 provides, to an image signal received from the camera head 105, various kinds of image processing for displaying an image based on the image signal, such as image development processing (demosaic processing). The CCU 139 provides the image signal provided with the image processing to the display device 141. In addition, the CCU 139 transmits a control signal to the camera head 105 and controls drive thereof. The control signal may include information related to image capturing conditions such as the magnification and the focal length.

Under control of the CCU 139, the display device 141 displays an image based on an image signal provided with image processing by the CCU 139. When the endoscope 101 can perform image capturing at high resolution such as 4 K (3840 horizontal pixels×2160 vertical pixels) or 8 K (7680 horizontal pixels×4320 vertical pixels) and/or can perform 3D display, the display device 141 used for the corresponding endoscope 101 may support high-resolution display and/or 3D display. When image capturing at high resolution such as 4 K or 8 K is supported, an enhanced sense of immersion can be obtained by using the display device 141 having a size of 55 inch or larger. Alternatively, a plurality of display devices 141 having resolutions and sizes different from each other may be provided in accordance with usage.

The light source device 143 includes a light source such as a light emitting diode (LED) and supplies irradiation light for image capturing of a surgery site to the endoscope 101.

The arm control device 145 includes a processor such as a CPU and operates in accordance with a predetermined computer program to control drive of the arm unit 131 of the support arm device 127 in accordance with a predetermined control scheme.

An input device 147 is an input interface for the endoscopic operation system 100. Through the input device 147, a user can input various kinds of information and instructions to the endoscopic operation system 100. For example, through the input device 147, the user inputs various kinds of information related to surgery, such as body information of the patient and information of the operative method of the surgery. In addition, through the input device 147, the user inputs an instruction to drive the arm unit 131, an instruction to change conditions (the kind, magnification, and focal length of irradiation light, and the like) of image capturing by the endoscope 101, an instruction to drive the energy treatment instrument 121, and the like.

The kind of the input device 147 is not limited, but the input device 147 may be one of various well-known input devices. Examples of the input device 147 include a mouse, a keyboard, a touch panel, a switch, a foot switch 157, and/or and a lever. When a touch panel is used as the input device 147, the touch panel may be provided on a display surface of the display device 141.

Alternatively, the input device 147 is a device mounted on the user, such as a glasses-type wearable device or a head mounted display (HMD), and various kinds of input are performed in accordance with the gesture and sight line of the user detected by these devices. The input device 147 includes a camera capable of detecting motion of the user, and various kinds of input are performed in accordance with the gesture and sight line of the user detected from a video captured by the camera. The input device 147 also includes a microphone capable of collecting voice of the user, and various kinds of input are performed by voice through the microphone. In this manner, since the input device 147 allows input of various kinds of information in a non-contact manner, the user (for example, the operator 167) belonging to a clean area, in particular, can operate an instrument belonging to an unclean area in a non-contact manner. In addition, the user can operate a held surgical instrument without removing a hand from the instrument, which improves convenience for the user.

A treatment instrument control device 149 controls drive of the energy treatment instrument 121 for tissue cauterization and incision, blood vessel sealing, and the like. A pneumoperitoneum device 151 expands the body cavity of the patient 171 by feeding gas into the body cavity through the pneumoperitoneum tube 119 to obtain a visual field through the endoscope 101 and a work space for the operator. A recorder 153 is a device capable of recording various kinds of information related to surgery. A printer 155 is a device capable of printing various kinds of information related to surgery in various formats of text, image, graph, and the like.

The following describes particularly characteristic configurations of the endoscopic operation system 100 in more detail.

(Support Arm Device)

The support arm device 127 includes the base unit 129 as a base, and the arm unit 131 extending from the base unit 129. In the illustrated example, the arm unit 131 includes the joint parts 133a, 133b, and 133c, and the links 135a and 135b coupled with each other through the joint part 133b, but the configuration of the arm unit 131 is illustrated in a simplified manner in FIG. 1 for simplification. In reality, the shape, number, and disposition of the joint parts 133a to 133c and the links 135a and 135b, the direction of a rotational axis of each of the joint parts 133a to 133c, and the like can be set as appropriate so that the arm unit 131 has a desired degree of freedom. For example, the arm unit 131 is preferably configured to have six degrees or more of freedom. Accordingly, the endoscope 101 can be freely moved in the movable range of the arm unit 131, and thus the lens barrel 103 of the endoscope 101 can be inserted into the body cavity of the patient 171 in a desired direction.

The joint parts 133a to 133c are each provided with an actuator and can be rotated about a predetermined rotational axis through drive of the actuator. The drive of the actuator is controlled by the arm control device 145 to control the rotation angle of each of the joint parts 133a to 133c and thus control drive of the arm unit 131. Accordingly, the position and posture of the endoscope 101 are controlled. In this case, the arm control device 145 can control drive of the arm unit 131 by various well-known control schemes such as force control and position control.

For example, when the operator 167 performs operation input as appropriate through the input device 147 (including the foot switch 157), drive of the arm unit 131 may be controlled as appropriate by the arm control device 145 in accordance with the operation input to control the position and posture of the endoscope 101. Through this control, the endoscope 101 at a leading end of the arm unit 131 can be moved from an optional position to another optional position and then be fixedly supported at the position after the movement. The arm unit 131 may be operated by what is called a master-slave scheme. In this case, the arm unit 131 can be remotely operated by the user through the input device 147 installed at a place separated from a surgery room.

When force control is applied, the arm control device 145 may perform what is called power assist control to drive the actuator of each of the joint parts 133a to 133c upon reception of external force from the user so that the arm unit 131 smoothly moves following the external force. Accordingly, when moving the arm unit 131 while directly touching the arm unit 131, the user can move the arm unit 131 with relatively light force. Thus, the endoscope 101 can be more intuitively moved through a simpler operation, which improves convenience for the user.

Typically, in an endoscopic operation, the endoscope 101 is supported by a doctor called scopist. When the support arm device 127 is used, however, the position of the endoscope 101 can be more reliably fixed in a non-manual manner, and thus an image of a surgery site can be reliably obtained and the surgery can be smoothly performed.

The arm control device 145 does not necessarily need to be provided to the cart 137. In addition, the arm control device 145 does not necessarily need to be one device. For example, the arm control device 145 may be provided to each of the joint parts 133a to 133c of the arm unit 131 of the support arm device 127, and the arm control devices 145 may cooperate with each other to achieve drive control of the arm unit 131.

(Light Source Device)

The light source device 143 supplies irradiation light for image capturing of a surgery site to the endoscope 101. The light source device 143 includes a white light source including, for example, an LED, a laser beam source, or combination thereof. In this case, when the white light source includes combination of RGB laser beam sources, the output intensity and output timing of each color (wavelength) can be highly accurately controlled, and thus the white balance of a captured image can be adjusted at the light source device 143. In addition, in this case, it is possible to irradiate an observation target with laser beams from the respective RGB laser beam sources in a time divisional manner and control drive of the image sensors of the camera head 105 in synchronization with the irradiation timings of the laser beams to capture images corresponding to the respective RGB colors in a time divisional manner. With this method, a color image can be obtained without providing color filters to the image sensors.

Drive of the light source device 143 may be controlled to change the intensity of output light in each predetermined time. Drive of the image sensors of the camera head 105 can be controlled in synchronization with the timing of the light intensity change to acquire images in a time divisional manner, and the images can be synthesized with one another to generate a high dynamic range image without what is called underexposure and overexposure.

The light source device 143 may be capable of supplying light in a predetermined wavelength band for special light observation. In the special light observation, for example, the wavelength dependency of light absorption in body tissue is used to perform what is called narrow band light observation (narrow band imaging) in which an image of a predetermined tissue such as a blood vessel on the surface layer of a mucous membrane is captured at high contrast through irradiation with light in a band narrower than that of irradiation light (which is white light) for normal observation. Alternatively, in the special light observation, fluorescence observation may be performed to obtain an image by fluorescence generated through irradiation with excitation light. In the fluorescence observation, for example, a body tissue is irradiated with excitation light and fluorescence from the body tissue is observed (autofluorescence observation), or a reagent such as indocyanine green (ICG) is locally injected into a body tissue and a fluorescence image is obtained by irradiating the body tissue with excitation light corresponding to a fluorescence wavelength of the reagent. The light source device 143 may be capable of supplying narrow band light and/or excitation light for such special light observation.

(Camera Head and CCU)

Functions of the camera head 105 and the CCU 139 of the endoscope 101 are described in more detail with reference to FIG. 2. FIG. 2 is a block diagram illustrating exemplary functional configurations of the camera head 105 and the CCU 139 illustrated in FIG. 1.

As illustrated in FIG. 2, the camera head 105 includes, as its functions, a lens unit 107, an image capturing unit 109, a drive unit 111, a communication unit 113, and a camera head control unit 115. The CCU 139 includes, as its functions, a communication unit 159, an image processing unit 161, and a control unit 163. The camera head 105 and the CCU 139 are connected with each other through a transmission cable 165 to perform bidirectional communication therebetween.

The following first describes a functional configuration of the camera head 105. The lens unit 107 is an optical system provided at a connection part with the lens barrel 103. The observation light acquired from the leading end of the lens barrel 103 is guided to the camera head 105 and incident on the lens unit 107. The lens unit 107 is a combination of a plurality of lenses including a zoom lens and a focus lens. The optical property of the lens unit 107 is adjusted to condense the observation light on the light-receiving surface of an image sensor of the image capturing unit 109. The positions of the zoom lens and the focus lens on an optical axis are movable for adjustment of the magnification and focal point of a captured image.

The image capturing unit 109 includes an image sensor and is disposed downstream of the lens unit 107. The observation light having passed through the lens unit 107 is condensed on the light-receiving surface of the image sensor, and an image signal corresponding to an observation image is generated through photoelectric conversion. The image signal generated by the image capturing unit 109 is provided to the communication unit 113.

The image sensor of the image capturing unit 109 is, for example, a complementary metal oxide semiconductor (CMOS) image sensor including a Bayer array and capable of performing color image capturing. Alternatively, the image sensor may be capable of capturing an image, for example, at a high resolution of 4 K or higher. Since an image of a surgery site can be obtained at high resolution, the operator 167 can understand the status of the surgery site in more detail and more smoothly proceed surgery.

The image sensor of the image capturing unit 109 includes one pair of image sensors for acquiring image signals for the right and left eyes, respectively for 3D display. When the 3D display is performed, the operator 167 can more accurately understand the depth of a living body tissue at a surgery site. When the image capturing unit 109 is a multiple plate type, a plurality of lens units 107 are provided for the respective image sensors.

The image capturing unit 109 does not necessarily need to be provided to the camera head 105. For example, the image capturing unit 109 may be provided right after the objective lens inside the lens barrel 103.

The drive unit 111 includes an actuator and moves each of the zoom and focus lenses of the lens unit 107 along the optical axis by a predetermined distance under control of the camera head control unit 115. Accordingly, the magnification and focal point of an image captured by the image capturing unit 109 can be adjusted as appropriate.

The communication unit 113 includes a communication device for transmitting and receiving various kinds of information to and from the CCU 139. The communication unit 113 transmits an image signal acquired from the image capturing unit 109 to the CCU 139 through the transmission cable 165 as RAW data. In this case, the image signal is preferably transmitted through optical communication to display a captured image of a surgery site at low latency. In a case of surgery, the operator 167 performs the surgery while observing the state of an affected part based on a captured image, and thus a moving image of the surgery site needs to be displayed in real time as much as possible for safer and more reliable surgery. When optical communication is to be performed, the communication unit 113 is provided with a photoelectric conversion module configured to convert an electric signal into an optical signal. The image signal is converted into an optical signal by the photoelectric conversion module and then transmitted to the CCU 139 through the transmission cable 165.

The communication unit 113 receives a control signal for controlling drive of the camera head 105 from the CCU 139. The control signal includes information related to image capturing conditions such as information for specifying the frame rate of a captured image, information for specifying the exposure value at image capturing, and/or information for specifying the magnification and focal point of the captured image. The communication unit 113 provides the received control signal to the camera head control unit 115. In addition, a control signal from the CCU 139 may be transmitted through optical communication. In this case, the communication unit 113 is provided with a photoelectric conversion module configured to convert an optical signal into an electric signal, and the control signal is converted into an electric signal by the photoelectric conversion module and then provided to the camera head control unit 115.

The above-described image capturing conditions such as the frame rate, the exposure value, the magnification, and the focal point are automatically set by the control unit 163 of the CCU 139 based on an acquired image signal. Accordingly, the endoscope 101 has what are called an auto exposure (AE) function, an auto focus (AF) function, and an auto white balance (AWB) function.

The camera head control unit 115 controls drive of the camera head 105 based on a control signal from the CCU 139 received through the communication unit 113. For example, the camera head control unit 115 controls drive of the image sensor of the image capturing unit 109 based on information for specifying the frame rate of a captured image and/or information for specifying the exposure at image capturing. In addition, for example, the camera head control unit 115 moves the zoom and focus lenses of the lens unit 107 as appropriate through the drive unit 111 based on information for specifying the magnification and focal point of a captured image. The camera head control unit 115 may also have a function to store information for identifying the lens barrel 103 and the camera head 105.

Components such as the lens unit 107 and the image capturing unit 109 can be disposed in a sealing structure having high air-tightness and waterproof properties to provide the camera head 105 with resistance against autoclave sterilization processing.

The following describes a functional configuration of the CCU 139. The communication unit 159 includes a communication device for transmitting and receiving various kinds of information to and from the camera head 105. The communication unit 159 receives an image signal transmitted from the camera head 105 through the transmission cable 165. In this case, as described above, the image signal is preferably transmitted through optical communication. In this case, to achieve optical communication, the communication unit 159 is provided with a photoelectric conversion module configured to convert an optical signal into an electric signal. The communication unit 159 provides the image signal converted into an electric signal to the image processing unit 161.

In addition, the communication unit 159 transmits a control signal for controlling drive of the camera head 105 to the camera head 105. The control signal may be transmitted through optical communication as well.

The image processing unit 161 provides various kinds of image processing to an image signal as RAW data transmitted from the camera head 105. Examples of the image processing include various kinds of well-known signal processing such as image development processing, image quality improvement processing (for example, band enhancement processing, super-resolution processing, noise reduction (NR) processing, and/or hand-shake correction processing), and/or enlargement processing (electronic zoom processing). The image processing unit 161 performs detection processing on the image signal for performing AE, AF, and AWB.

The image processing unit 161 includes a processor such as a CPU or a GPU, and the processor operates in accordance with a predetermined computer program to perform the above-described image processing or detection processing. When the image processing unit 161 includes a plurality of GPUs, the image processing unit 161 divides information related to an image signal as appropriate, and the GPUs performs image processing on the divided information in parallel.

The control unit 163 performs various kinds of control related to image capturing of a surgery site by the endoscope 101 and display of an image thus captured. For example, the control unit 163 generates a control signal for controlling drive of the camera head 105. In this case, when image capturing conditions are input by the user, the control unit 163 generates the control signal based on the input by the user. Alternatively, when the endoscope 101 has an AE function, an AF function, and an AWB function, the control unit 163 generates the control signal by calculating optimum exposure value, focal length, and white balance as appropriate in accordance with a result of detection processing performed by the image processing unit 161.

The control unit 163 controls the display device 141 to display the image of the surgery site based on an image signal provided with image processing by the image processing unit 161. In this case, the control unit 163 recognizes various objects in the surgery site image by using various image recognition technologies. For example, the control unit 163 can recognize surgical instruments such as forceps, a particular living body site, bleeding, mist when the energy treatment instrument 121 is used, and the like by detecting, for example, an edge shape and color of any object included in the surgery site image. When controlling the display device 141 to display the image of the surgery site, the control unit 163 displays various kinds of surgery support information in a superimposed manner on the image of the surgery site by using a result of the recognition. When the surgery support information is displayed in a superimposed manner and presented to the operator 167, surgery can be proceeded in a safer and more reliable manner.

The transmission cable 165 connecting the camera head 105 and the CCU 139 is an electric signal cable for electric signal communication, an optical fiber for optical communication, or a composite cable thereof.

In the illustrated example, communication is performed in a wired manner by using the transmission cable 165, but communication between the camera head 105 and the CCU 139 may be performed in a wireless manner. When communication between both members is performed in a wireless manner, the transmission cable 165 does not need to be laid in the surgery room, thus a situation of interference of the transmission cable 165 with movement of medical staff in the surgery room can be solved.

The above description is made on an example of the endoscopic operation system 100 to which the technology according to the present disclosure is applicable. Although the endoscopic operation system 100 is described as an example above, a system to which the technology according to the present disclosure is applicable is not limited to such an example. For example, the technology according to the present disclosure may be applied to an examination flexible endoscope system or a microscopic operation system.

2. TECHNICAL PROBLEM

The following describes technical problems of a medical observation system according to an embodiment of the present disclosure.

At a medical site, it is assumed that an aged surgeon is retired from surgery due to physical problem. However, a junior surgeon often takes time to become independent because surgery experience is needed. With such a background, it is assumed that the number of surgeons (in particular, experienced veteran surgeons) is insufficient and a junior surgeon performs surgery while being instructed by an aged surgeon.

However, it is sometimes difficult for an aged surgeon retired from surgery due to physical problem to attend surgery. With such a background, it has been required to introduce a technology with which a surgeon who instructs a surgeon (operating surgeon) such as a junior surgeon in charge of manipulation can perform the instruction without attending surgery, thereby reducing a load on the surgeon performing the instruction.

To fulfill such a requirement, the present disclosure provides a technology with which a task cooperatively performed by a plurality of doctors spatially isolated from each other can be achieved in a more preferable aspect. Specifically, an exemplary technology that can achieve, in a more preferable aspect, arrangement with which a doctor (for example, a junior surgeon) performing manipulation in a surgery room can be instructed by another doctor (for example, an aged surgeon) in a room different from the surgery room is disclosed.

3. TECHNOLOGICAL CHARACTERISTICS

The following describes technological characteristics of the medical observation system according to an embodiment of the present disclosure.

3.1. SYSTEM CONFIGURATION

Figure 3:
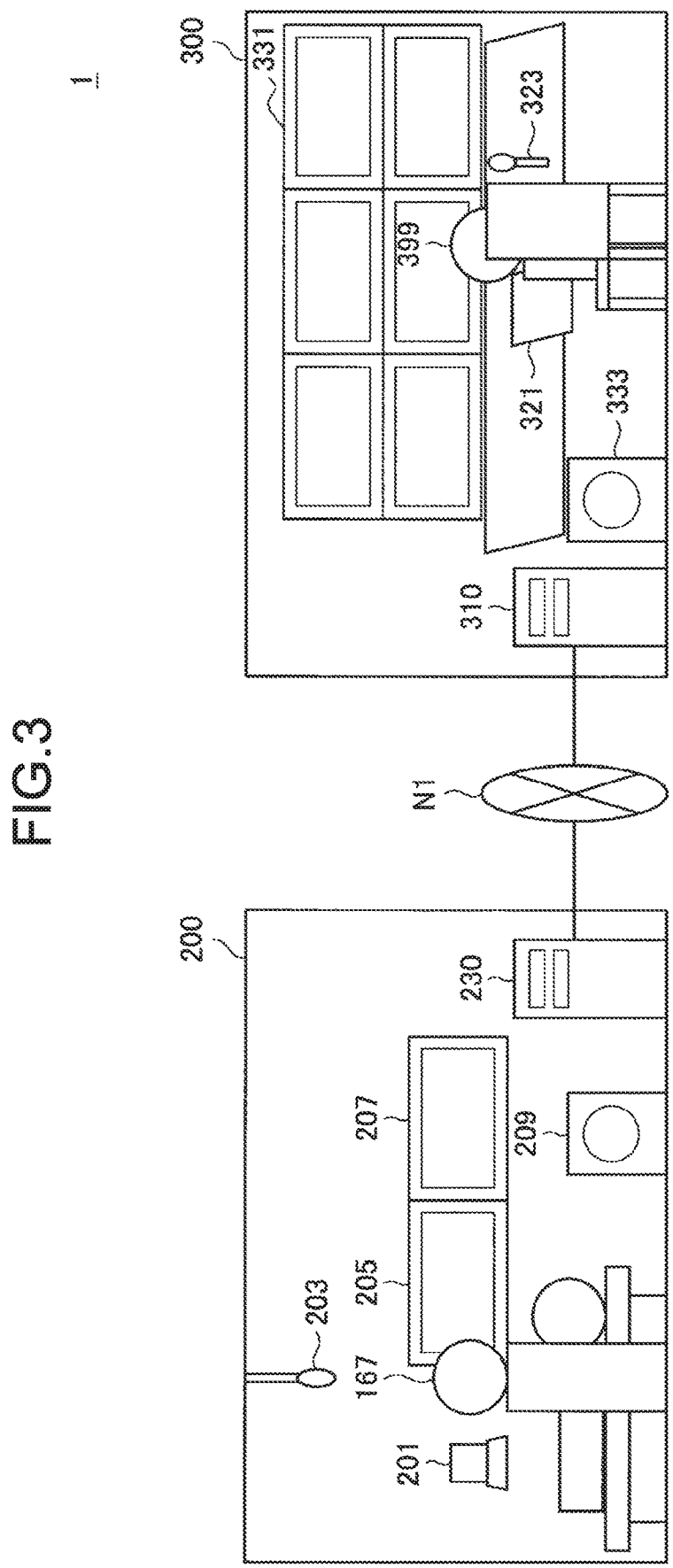
FIG. 3 is an explanatory diagram for describing an exemplary system configuration of a medical observation system according to an embodiment of the present disclosure.

The following first describes an exemplary system configuration of the medical observation system according to an embodiment of the present disclosure with reference to FIG. 3. FIG. 3 is an explanatory diagram for describing the exemplary system configuration of the medical observation system according to the present embodiment.

As illustrated in FIG. 3, a medical observation system 1 according to the present embodiment is configured based on an assumption of a situation including an operator (doctor) 167 performing manipulation of surgery in a surgery room and an instructor (doctor) 399 who provides various instructions to the operator 167 (or an operation team member who performs treatment together with the operator) from the outside of the surgery room (from an instruction room). Specifically, in the medical observation system 1, a system 200 on the surgery room side and a system 300 on the instruction room side are connected with each other through a predetermined network N1. The system 200 on the surgery room side corresponds to what is called a medical observation system (in other words, a surgery system) such as the endoscopic operation system 100 described with reference to FIGS. 1 and 2. The system 300 on the instruction room side is a system for the instructor 399 in the instruction room to check the situation of surgery being performed in the surgery room and provide various instructions to the operator 167 performing manipulation in the surgery room. In the following description, the system 200 on the surgery room side is also referred to as a "first system 200", and the system 300 on the instruction room side is also referred to as a "second system 300".

The following first describes the first system 200. As illustrated in FIG. 3, the first system 200 includes, for example, an image capturing device 201, a sound collection device 203, display devices 205 and 207, an audio output device 209, and an information processing device 230. Although not illustrated in FIG. 3, the first system 200 may include a detection device (for example, a sensor) for detecting various states (for example, a vital state) of a patient, various states of the surgery room, and the like. In addition, the first system 200 may include any component included in a medical observation system (in other words, a surgery system) applied as the first system 200, such as the endoscopic operation system 100 described with reference to FIGS. 1 and 2, in accordance with the type of the medical observation system.

The image capturing device 201 corresponds to an operation place camera configured to capture an image of the situation of the surgery room, an operation field camera configured to capture an image of an operation field, and the like. When the first system 200 is configured as the endoscopic operation system 100 described with reference to FIGS. 1 and 2, for example, the image capturing device 201 may correspond to an image capturing device, such as the endoscope 101, configured to capture an image of an affected part. A plurality of image capturing devices such as the operation place camera, the operation field camera, and the endoscope 101 described above may be provided as the image capturing device 201. In the following description, for sake of simplicity, the term "image capturing device 201" may include one or more image capturing devices (for example, the operation place camera, the operation field camera, and the endoscope 101 described above) unless otherwise stated.

The sound collection device 203 is configured as what is called a microphone and collects audio in the surgery room. The sound collection device 203 may be configured to collect voice of the operator 167. In this case, for example, the sound collection device 203 may be configured as a microphone having directionality. As another example, the sound collection device 203 may be configured as a microphone held by a head set mounted on the operator 167. With such a configuration, for example, voice of the operator 167 can be presented to the instructor 399 on the instruction room side by forwarding a result of sound collection of the voice by the sound collection device 203 to the second system 300 through the network N1.

The audio output device 209 is configured as what is called a speaker and outputs audio such as voice. For example, the audio output device 209 may output voice of the instructor 399 based on audio data corresponding to a result of sound collection of the voice acquired by the second system 300. With such a configuration, the voice of the instructor 399 on the instruction room side can be presented to the operator 167. The audio output device 209 may be configured as a head set (in other words, headphones) mounted on the operator 167.

Each of the display devices 205 and 207 is configured as what is called a display and displays display information such as an image to present the display information to the user (for example, the operator 167). At least one of the display devices 205 and 207 may display, for example, an image corresponding to a result of image capturing of the operation field by the image capturing device 201 configured as an operation field camera, and an image corresponding to a result of image capturing of an affected part by the image capturing device 201 configured as the endoscope 101. In addition, at least one of the display devices 205 and 207 may display, for example, information in accordance with an instruction from the instructor 399 through the second system 300.

The information processing device 230 may be configured as what is called a medical signal processing device. As a specific example, the information processing device 230 may provide predetermined signal processing to image data corresponding to a result of image capturing (for example, a result of image capturing of the operation field or an affected part) by the image capturing device 201 and control at least one of the display devices 205 and 207 to display an image corresponding to the image data provided with the signal processing. Thus, the information processing device 230 may correspond to, for example, the camera control unit (CCU) 139 illustrated in FIGS. 1 and 2. Accordingly, the information processing device 230 can present an image obtained by providing the above-described signal processing to the result of image capturing by the image capturing device 201 to the operator 167 through a predetermined display device (for example, the display device 205 or 207). The information processing device 230 corresponds to an exemplary "first medical signal processing device". The operator 167 corresponds to an exemplary "first user". The first user as a user on the first system 200 side may correspond to an exemplary "user associated with the first medical signal processing device".

The information processing device 230 may have a communication function to transmit and receive various kinds of information to and from a predetermined component (for example, an information processing device 310 to be described later) on the second system 300 side through the network N1. With such a configuration, for example, the information processing device 230 may transmit image data corresponding to a result of image capturing by the image capturing device 201 (for example, the image data is RAW data corresponding to a result of image capturing by an endoscope or the like), or image data obtained by providing predetermined processing to the image data, to a predetermined component on the second system 300 side. Details of exemplary predetermined processing provided to image data corresponding to a result of image capturing by the image capturing device 201 will be described later separately. For example, the information processing device 230 may acquire, from a predetermined component on the second system 300 side, information in accordance with an instruction from the instructor 399, and may present the acquired information to the operator 167 through the display devices 205 and 207 and the audio output device 209.

The information processing device 230 may be capable of controlling at least part of the operation of a predetermined medical device such as an energy device. With such a configuration, for example, the information processing device 230 may control the operation of the predetermined medical device in accordance with control by a predetermined component (for example, the information processing device 310) on the second system 300 side through the network N1. With such a configuration, for example, the instructor 399 can operate the second system 300 in the instruction room to temporarily control (for example, stop or restrict) the operation of the predetermined medical device used by the operator 167 in the surgery room.

Details of the configuration of the information processing device 230 will be described later separately.

The following describes the second system 300. As illustrated in FIG. 3, the second system 300 includes, for example, the information processing device 310, an input device 321, a sound collection device 323, a display device 331, and an audio output device 333.

The input device 321 is a component through which the user (for example, the instructor 399) inputs various kinds of information to a predetermined component (for example, the information processing device 310) on the second system 300 side. The input device 321 may be configured as an input device such as a touch panel, a mouse, a keyboard, or a switch. The input device 321 is not limited to a particular configuration but only needs to have a configuration through which the user can input desired information to the predetermined component on the second system 300 side.

The sound collection device 323 is configured as what is called a microphone and collects audio in the instruction room. The sound collection device 323 may be configured to collect voice of the instructor 399. In this case, the sound collection device 323 may be configured as a microphone held by a head set mounted on the instructor 399. With such a configuration, for example, voice of the instructor 399 can be presented to the operator 167 on the surgery room side by forwarding a result of sound collection of the voice by the sound collection device 323 to the first system 200 through the network N1.

The audio output device 333 is configured as what is called a speaker and outputs audio such as voice. For example, the audio output device 333 may output voice of the operator 167 based on audio data corresponding to a result of sound collection of the voice acquired by the first system 200. With such a configuration, the voice of the operator 167 on the surgery room side can be presented to the instructor 399. The audio output device 333 may be configured as a head set (in other words, headphones) mounted on the instructor 399.

The display device 331 is configured as what is called a display and displays display information such as an image to present the display information to the user (for example, the instructor 399). The display device 331 may display, for example, an image corresponding to a result of image capturing by the image capturing device 201, which is forwarded from the first system 200 through the network N1. The display device 331 may display an image in accordance with a result of predetermined signal processing performed on image data corresponding to the result of image capturing by the image capturing device 201 by the information processing device 310 to be described later. A plurality of display devices 331 may be provided. In this case, the display devices 331 may be configured to display pieces of information different from each other. Two or more of the display devices 331 may be used as one display region, and a series of pieces of display information may be displayed across the two or more display devices 331. In the following description, for sake of simplicity, the term "display device 331" may include one or more display devices unless otherwise stated.

The information processing device 310 may have a communication function to transmit and receive various kinds of information to and from a predetermined component (for example, the information processing device 230) on the first system 200 side through the network N1. With such a configuration, for example, the information processing device 310 may acquire image data corresponding to a result of image capturing by the image capturing device 201 from the predetermined component on the first system 200 side. Accordingly, the information processing device 310 can present an image (in other words, an image corresponding to the result of image capturing by the image capturing device 201) corresponding to the acquired image data to the instructor 399 through the display device 331.

The information processing device 310 may be configured as what is called a medical signal processing device. Specifically, the information processing device 310 may provide predetermined signal processing to image data acquired from a predetermined component on the first system 200 side (which is image data corresponding to a result of image capturing by the image capturing device 201, or image data obtained by providing predetermined processing to the image data) and control the display device 331 to display an image corresponding to the image data provided with signal processing. In addition, the information processing device 310 may control the signal processing provided to the above-described image data in accordance with an instruction from the instructor 399 through the input device 321. The information processing device 310 corresponds to an exemplary "second medical signal processing device". The instructor 399 corresponds to an exemplary "second user". The second user as a user on the second system 300 side may correspond to an exemplary "user associated with the second medical signal processing device".

The information processing device 310 may be capable of controlling at least part of the operation of a predetermined component on the first system 200 side (for example, the information processing device 230) through the network N1.

Details of the configuration of the information processing device 310 will be described later separately.

The following describes an exemplary system configuration of the medical observation system according to an embodiment of the present disclosure with reference to FIG. 3.

3.2. FUNCTIONAL CONFIGURATION

Figure 4:
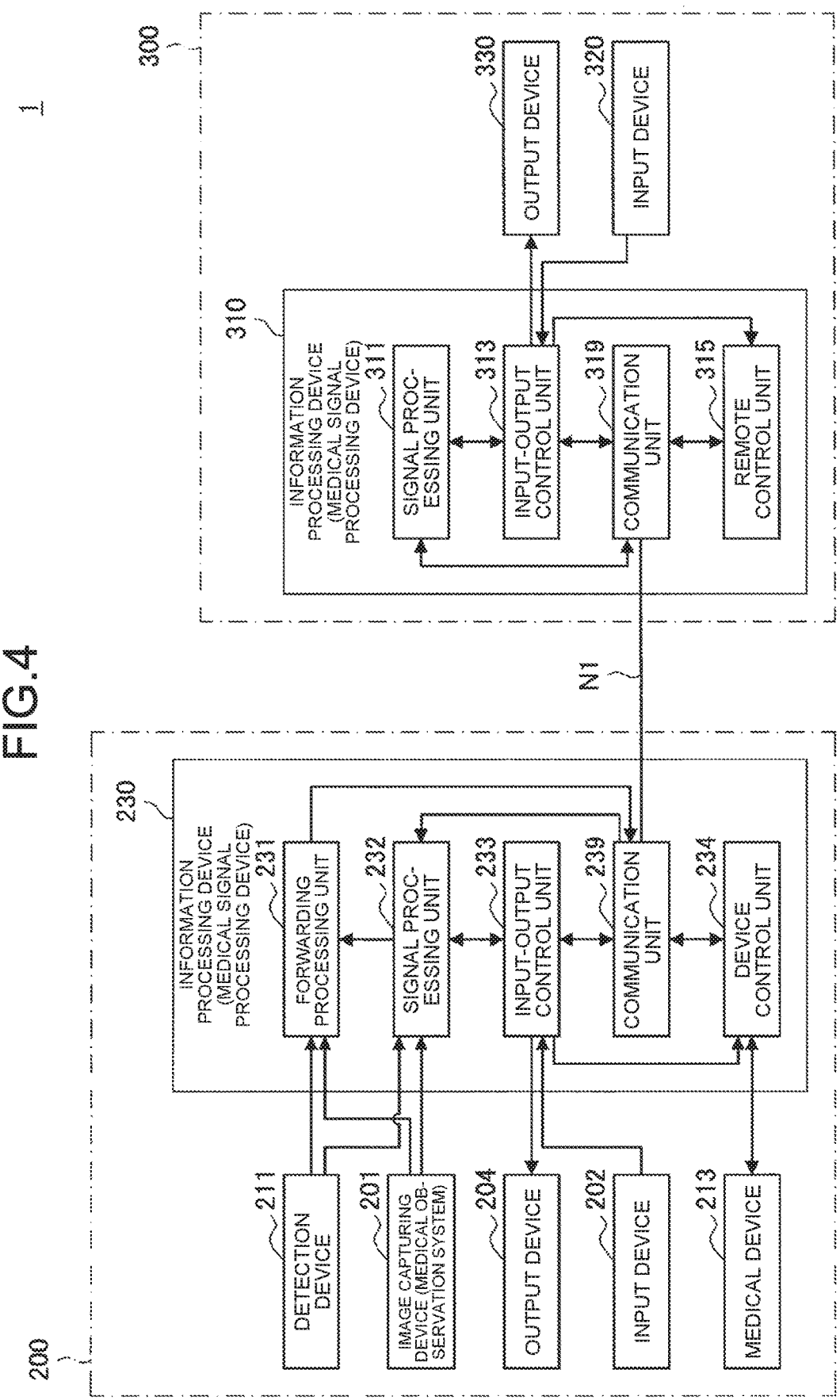
FIG. 4 is a block diagram illustrating an exemplary functional configuration of the medical observation system according to the present embodiment.

The following describes an exemplary functional configuration of the medical observation system according to an embodiment of the present disclosure with reference to FIG. 4. FIG. 4 is a block diagram illustrating the exemplary functional configuration of the medical observation system according to the present embodiment. In the example illustrated in FIG. 4, the medical observation system 1 includes the first system 200 on the surgery room side and the second system 300 on the instruction room side as described with reference to FIG. 3.

The following first describes the first system 200. As illustrated in FIG. 4, the first system 200 includes the image capturing device 201, an input device 202, an output device 204, and the information processing device 230. The first system 200 may also include a detection device 211 and a medical device 213.

The image capturing device 201 corresponds to the image capturing device 201 illustrated in FIG. 3. Thus, the image capturing device 201 may correspond to a medical observation device such as an endoscope or a surgical microscope. The input device 202 corresponds to a component for inputting various kinds of information to the information processing device 230 and may include, for example, the sound collection device 203 illustrated in FIG. 3. The output device 204 corresponds to a component for presenting various kinds of information to the user (for example, the operator 167 illustrated in FIG. 3) and may include, for example, the display devices 205 and 207 and the audio output device 209 illustrated in FIG. 3. The output device 204 corresponds to an exemplary "first output unit" in the present embodiment.

The medical device 213 schematically indicates a device (for example, an energy device) used by a doctor (for example, the operator 167 illustrated in FIG. 3) performing various kinds of manipulation in surgery to perform the manipulation. In addition, an instruction device (for example, a pointer) configured to emit light to at least part of an affected part as a treatment target in surgery to present the light as an index to at least part of the affected part may be included as the medical device 213. For example, the instruction device may be held by the image capturing device 201 (which is a medical observation device) such as an endoscope. With such a configuration, the operation of the instruction device can be controlled to project light as an index to part of an object (for example, an affected part) in the image capturing range of the image capturing device 201.

The detection device 211 includes various sensors and the like and schematically indicates a device configured to detect a predetermined state. As a specific example, the detection device 211 may be configured to detect various states in the surgery room. The detection device 211 may be configured to detect various states (for example, the vital state) of the patient.

The information processing device 230 includes a forwarding processing unit 231, a signal processing unit 232, an input-output control unit 233, a device control unit 234, and a communication unit 239.

The communication unit 239 is a communication interface through which the information processing device 230 transmits and receives various kinds of information to and from another device (for example, the information processing device 310 on the second system 300 side) through the predetermined network N1. The configuration of the communication unit 239 may be changed as appropriate in accordance with the scheme of communication with the other device. In the following description, when a component in the information processing device 230 transmits and receives information to and from another device (for example, the information processing device 310), the information is transmitted and received through the communication unit 239 unless otherwise stated.

The forwarding processing unit 231 forwards various kinds of information acquired in the first system 200 to the information processing device 310 on the second system 300 side through the network N1. As a specific example, the forwarding processing unit 231 may forward image data corresponding to a result of image capturing of an object (for example, the operation place, the operation field, or an affected part) by the image capturing device 201 to the information processing device 310. In this case, the forwarding processing unit 231 may forward the above-described image data provided with desired signal processing by the signal processing unit 232 to be described later to the information processing device 310. As another example, the forwarding processing unit 231 may forward various kinds of information corresponding to a result of detection of a predetermined state (for example, the vital state of the patient) by the detection device 211 to the information processing device 310. In this case, the forwarding processing unit 231 may forward various kinds of information corresponding to a result of the detection provided with desired signal processing by the signal processing unit 232 to the information processing device 310.

The signal processing unit 232 provides various kinds of signal processing (in other words, image processing) to image data corresponding to a result of image capturing of an object by the image capturing device 201. In the following description, image data not provided with the signal processing is also referred to as "RAW data". Examples of the signal processing include minimum signal processing (hereinafter also referred to as "RAW processing") provided to display an image based on image data, such as defect pixel correction, and signal processing selectively provided as necessary, such as image quality improvement processing, enlargement processing, and superimposition processing.

The signal processing unit 232 may acquire, from the information processing device 310 on the second system 300 side, information related to signal processing provided to image data by the information processing device 310, and may provide signal processing in accordance with the acquired information to image data held by the signal processing unit 232.

Then, the signal processing unit 232 may output image data provided with at least part of the above-described signal processing to the input-output control unit 233. Accordingly, the input-output control unit 233 can present an image corresponding to the image data to the user (for example, the operator 167 illustrated in FIG. 3) through the output device 204. The signal processing unit 232 may instruct the forwarding processing unit 231 to forward image data provided with at least part (for example, the RAW processing) of the above-described signal processing to the information processing device 310 on the second system 300 side.

The signal processing unit 232 may provide predetermined signal processing to various kinds of information corresponding to a result of detection of a predetermined state (for example, the vital state of the patient) by the detection device 211. At least part of the signal processing on at least part of the various kinds of information may be selectively applied in accordance with an instruction from a predetermined user (for example, an anesthesiologist) through the input device 202. In this case, for example, the signal processing unit 232 may provide signal processing to at least part of information in accordance with a result of recognition, by the input-output control unit 233 to be described later, of a content instructed by the user. This is same for above-described signal processing on image data. In addition, similarly to the above-described case of image data, in accordance with signal processing provided to information corresponding to a result of detection of a predetermined state by the information processing device 310 on the second system 300 side, the signal processing unit 232 may provide signal processing to the information held by the signal processing unit 232.

Then, the signal processing unit 232 may output information provided with at least part of the above-described signal processing (in other words, information corresponding to results of detection of various states) to the input-output control unit 233. Accordingly, the input-output control unit 233 can present the information corresponding to the results of detection of various states by the detection device 211 to a user (for example, the operator 167 illustrated in FIG. 3) through the output device 204. The signal processing unit 232 may instruct the forwarding processing unit 231 to forward information provided with at least part of the above-described signal processing to the information processing device 310 on the second system 300 side.

The input-output control unit 233 analyzes input information from the user through the input device 202 and recognizes a content instructed by the user based on a result of the analysis. As a specific example, the input-output control unit 233 may provide voice recognition processing and natural language processing to a result of sound collection of voice of the user by the input device 202 configured as a sound collection unit to recognize a content spoken by the user (in other words, a content instructed by the user). Then, the input-output control unit 233 may perform control to execute processing in accordance with a result of recognition of the content instructed by the user. As a specific example, the input-output control unit 233 may instruct the signal processing unit 232 to control signal processing. In addition, the input-output control unit 233 may instruct the device control unit 234 to be described later to control the operation of the medical device 213.

The input-output control unit 233 may acquire image data provided with signal processing from the signal processing unit 232 and control the output device 204 to output an image corresponding to the image data. Accordingly, the input-output control unit 233 can present the image to the user through the output device 204. Similarly, the input-output control unit 233 may acquire information corresponding to a result of detection of a predetermined state, which is provided with signal processing from the signal processing unit 232, and control the output device 204 to output the information. Accordingly, the input-output control unit 233 can present the information corresponding to a result of detection of a predetermined state (for example, the vital state of the patient) to the user through the output device 204. The input-output control unit 233 corresponds to an exemplary "first output control unit".

The device control unit 234 controls the operation of the medical device 213. As a specific example, the device control unit 234 may control the operation of the medical device 213 in accordance with an instruction from the user through the input device 202. In this case, the device control unit 234 may control the operation of the medical device 213 in accordance with a result of recognition, by the input-output control unit 233, of a content instructed by the user. As another example, the device control unit 234 may control at least some of various kinds of the operation of the medical device 213 in accordance with an instruction from the information processing device 310 on the second system 300 side.

The following describes the second system 300. As illustrated in FIG. 4, the second system 300 includes an input device 320, an output device 330, and the information processing device 310.

The input device 320 corresponds to a component for inputting various kinds of information to the information processing device 310 and may include, for example, the input device 321 and the sound collection device 323 illustrated in FIG. 3. The output device 330 corresponds to a component for presenting various kinds of information to a user (for example, the instructor 399 illustrated in FIG. 3) and may include, for example, the display device 331 and the audio output device 333 illustrated in FIG. 3. The output device 330 corresponds to an exemplary "second output unit" in the present embodiment.

The information processing device 310 includes a signal processing unit 311, an input-output control unit 313, a remote control unit 315, and a communication unit 319.

The communication unit 319 is a communication interface through which the information processing device 310 transmits and receives various kinds of information to and from another device (for example, the information processing device 230 on the first system 200 side) through the predetermined network N1. The configuration of the communication unit 319 may be changed as appropriate in accordance with the scheme of communication with the other device. In the following description, when a component in the information processing device 310 transmits and receives information to and from another device (for example, the information processing device 230), the information is transmitted and received through the communication unit 319 unless otherwise stated.

The signal processing unit 311 acquires image data corresponding to a result of image capturing of an object by the image capturing device 201 on the first system 200 side from the information processing device 230, and provides various kinds of signal processing (in other words, image processing) to the acquired image data. An example of the signal processing is same as that for the signal processing unit 232, and thus detailed description thereof will be omitted. At least part of the signal processing on the image data may be selectively applied in accordance with an instruction from a predetermined user (for example, the instructor 399 illustrated in FIG. 3) through the input device 320. In this case, for example, the signal processing unit 311 may provide signal processing to the image data in accordance with a result of recognition, by the input-output control unit 313 to be described later, of a content instructed by the user.

Then, the signal processing unit 311 outputs the above-described image data provided with signal processing to the input-output control unit 313. Accordingly, the input-output control unit 313 can present an image corresponding to the image data to the user (for example, the instructor 399 illustrated in FIG. 3) through the output device 330.

The signal processing unit 311 may acquire various kinds of information corresponding to a result of detection of a predetermined state (for example, the vital state of the patient) by the detection device 211 on the first system 200 side from the information processing device 230, and may provide various kinds of signal processing to the acquired various kinds of information. At least part of the signal processing on at least part of the various kinds of information may be selectively applied in accordance with an instruction from a predetermined user (for example, the instructor 399 illustrated in FIG. 3) through the input device 320. In this case, for example, the signal processing unit 311 may provide signal processing to at least part of information in accordance with a result of recognition, by the input-output control unit 313 to be described later, of a content instructed by the user.

Then, the signal processing unit 311 outputs the above-described information (in other words, information corresponding to results of detection of various states) provided with the signal processing to the input-output control unit 313. Accordingly, the input-output control unit 313 can present the information corresponding to the results of detection of various states (for example, the vital state of the patient) by the detection device 211 on the first system 200 side to the user (for example, the instructor 399 illustrated in FIG. 3) through the output device 330.

The signal processing unit 311 may transmit information related to at least part of various kinds of signal processing provided to information corresponding to a result of detection of image data and a predetermined state to the information processing device 230 (signal processing unit 232) through the network N1. With such a configuration, for example, the information processing device 230 (signal processing unit 232) can recognize the content of signal processing provided to the image data by the signal processing unit 311 and provide signal processing in accordance with a result of the recognition to image data held by the information processing device 230. This is same for the information corresponding to a result of detection of a predetermined state.

The input-output control unit 313 analyzes input information from the user through the input device 320 and recognizes a content instructed by the user based on a result of the analysis. The method of recognizing the content instructed by the user is same as that for the input-output control unit 233 described above, and thus detailed description thereof will be omitted. Then, the input-output control unit 313 may perform control to execute processing in accordance with a result of recognition of the content instructed by the user. As a specific example, the input-output control unit 313 may instruct the signal processing unit 311 to control signal processing. In addition, the input-output control unit 313 may instruct a device control unit 315 to be described later to control the operation of the medical device 213 on the first system 200 side through the network N1.

The input-output control unit 313 may acquire image data provided with signal processing from the signal processing unit 311 and control the output device 330 to output an image corresponding to the image data. Accordingly, the input-output control unit 313 can present the image to the user through the output device 330. Similarly, the input-output control unit 313 may acquire information corresponding to a result of detection of a predetermined state, which is provided with signal processing from the signal processing unit 311, and control the output device 330 to output the information. Accordingly, the input-output control unit 313 can present the information corresponding to a result of detection of a predetermined state (for example, the vital state of the patient) to the user through the output device 330. The input-output control unit 313 corresponds to an exemplary "second output control unit".

The remote control unit 315 controls the operation of the medical device 213 on the first system 200 side through the network N1. As a specific example, the remote control unit 315 may indirectly control the operation of the medical device 213 through the information processing device 230 by transmitting an instruction related to control of the operation of the medical device 213 to the information processing device 230 (the device control unit 234). In this case, the remote control unit 315 may control the operation of the medical device 213 in accordance with an instruction from the user through the input device 320. In this case, the remote control unit 315 may control the operation of the medical device 213 in accordance with a result of recognition of a content instructed by the user by the input-output control unit 313.

The above-described functional configuration of the medical observation system 1 is merely exemplary and not necessarily limited to the example illustrated in FIG. 4 as long as each component can operate as described above. For example, two or more of the components included in the first system 200 may be integrally configured. In addition, some of the components of the information processing device 230 may be provided outside the information processing device 230. As a specific example, the device control unit 234 may be provided to a device (control device) different from the information processing device 230. In addition, each function of the information processing device 230 may be achieved by a plurality of devices operating in cooperation. Each example described above is same for the second system 300 side.

The exemplary functional configuration of the medical observation system according to an embodiment of the present disclosure is described above with reference to FIG. 4.

3.3. EXAMPLES

The following describes, as examples, exemplary operation of the medical observation system according to an embodiment of the present disclosure.

Example 1

The following first describes, as Example 1, exemplary control for the instructor 399 to instruct, in a more preferable aspect from the outside of the surgery room (from the instruction room), the operator 167 performing manipulation on the surgery room side in a system configuration as illustrated in FIG. 3.

Specifically, in Example 1, various kinds of information acquired in the first system 200 on the surgery room side is forwarded to the second system 300 on the instruction room side and presented to the instructor 399 in the instruction room. When the instructor 399 inputs various kinds of information to the presented information through an input device, this input content is forwarded from the second system 300 to the first system 200 side and reflected on information presented to the operator 167 by the first system 200. Accordingly, the operator 167 can recognize an instruction (intention) from the instructor 399 based on the information reflected, through an operation by the instructor 399, on the information (for example, an image of the operation place or the operation field) referred to by the operator 167. The following describes exemplary operation of the medical observation system according to Example 1 in detail with reference to FIGS. 5 and 6.

Figure 5:
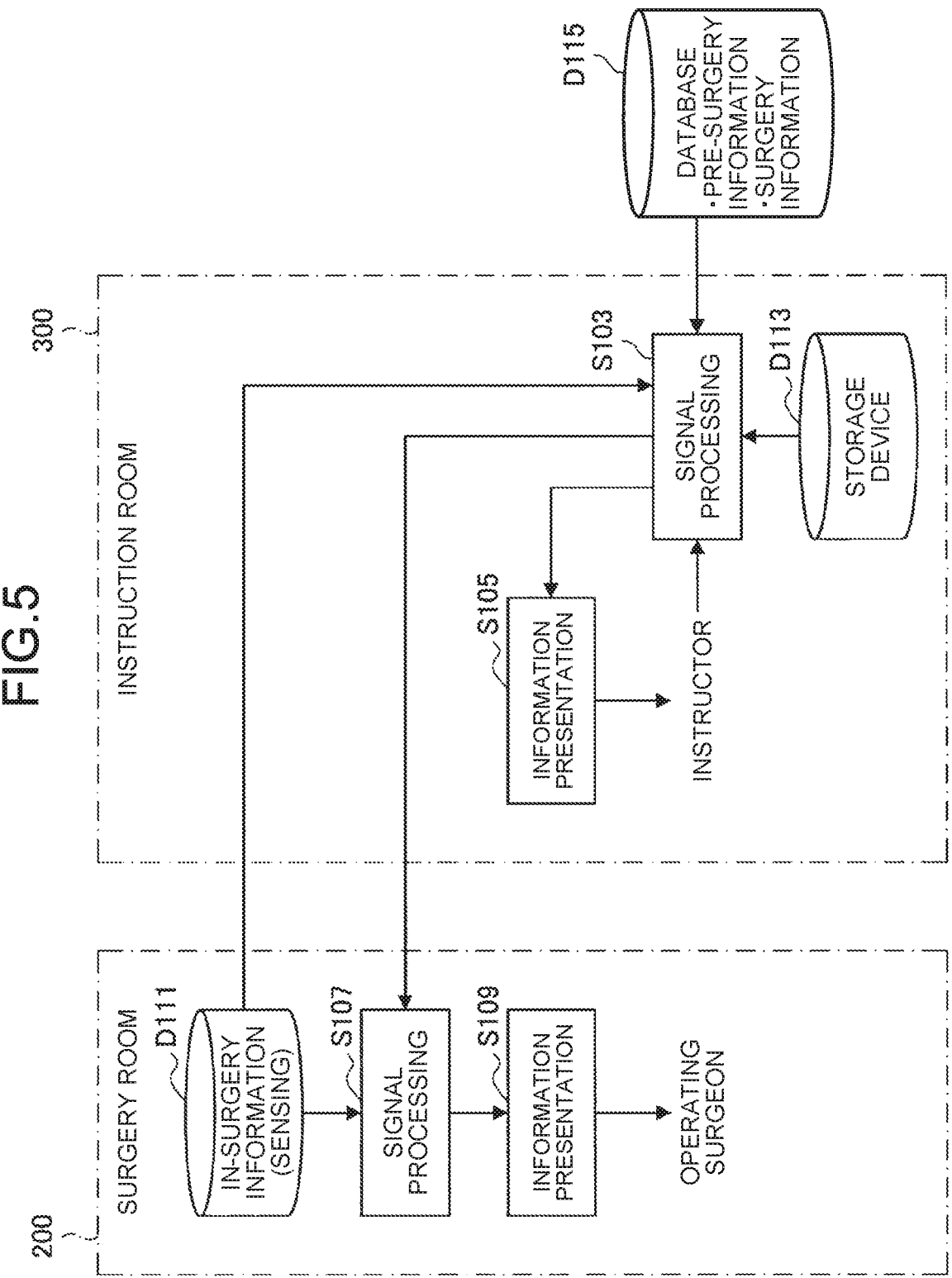
FIG. 5 is an explanatory diagram for describing an exemplary procedure of a series of processing at the medical observation system according to Example 1.

The following first describes an exemplary procedure of a series of processing at the medical observation system according to Example 1 with reference to FIG. 5, with a focus on flow of information, in particular. FIG. 5 is an explanatory diagram for describing the exemplary procedure of a series of processing at the medical observation system according to Example 1.

In FIG. 5, Reference sign D111 schematically indicates information (hereinafter also referred to as "in-surgery information") acquired in surgery. Examples of the in-surgery information D111 include image data corresponding to a result of image capturing by the image capturing device 201, audio data (voice data) corresponding to a result of sound collection by the sound collection device 203, and information corresponding to a result of detection by the detection device 211. In the present description, for clear understanding of characteristics of the medical observation system according to Example 1, the following description assumes that the in-surgery information D111 is image data corresponding to a result of image capturing by the image capturing device 201. Thus, hereinafter, the in-surgery information D111 illustrated in FIG. 5 is also referred to as "image data D111". In addition, in the present disclosure, image data, audio data (voice data), information corresponding to a result of detection by the detection device 211, and the like, which can be acquired as the above-described in-surgery information, are also collectively referred to as "medical data".

As illustrated in FIG. 5, the image data D111 is forwarded from the first system 200 on the surgery room side to the second system 300 on the instruction room side through the predetermined network N1. In this case, a copy of the image data D111 acquired in the first system 200 is forwarded to the second system 300 so that the image data D111 is held in each of the first system 200 and the second system 300. Thus, in the following description, for sake of simplicity, the image data D111 held on the first system 200 side is also referred to as "image data D111a", and the image data D111 held on the second system 300 side (which is the image data D111 forwarded to the second system 300) is also referred to as "image data D111b". When not distinguished from each other, in particular, the image data D111a and D111b are simply referred to as "the image data D111". In addition, the image data D111a held on the first system 200 side corresponds to exemplary "first image data", and the image data D111b held on the second system 300 side corresponds to exemplary "second image data".

The following describes an exemplary procedure of processing on the second system 300 side. In the second system 300, the information processing device 310 (signal processing unit 311) provides various kinds of signal processing to the image data D111b forwarded from the information processing device 230 on the first system 200 side (S103). In this case, the information processing device 310 may use, in the signal processing, information (for example, pre-surgery information and surgery information) held in an external database D115. In addition, the information processing device 310 may temporarily or permanently store the acquired image data D111b in a storage device D113 and provide the above-described signal processing to the image data D111b stored in the storage device D113. In addition, the information processing device 310 may store the image data D111b provided with the signal processing in the storage device D113. Then, the information processing device 310 (input-output control unit 313) presents an image based on the image data D111b provided with the signal processing to the user (instructor 399) on the instruction room side through the output device 330 (S105). The signal processing provided to the image data D111b by the information processing device 310 corresponds to an exemplary "second signal processing".

The information processing device 310 (signal processing unit 311) may receive an instruction from the instructor 399 through the input device 320 and provide signal processing in accordance with the instruction to the image data D111b (S103). In this case, the information processing device 310 (input-output control unit 313) may present an image based on the image data D111b provided with the signal processing to the instructor 399 through the output device 330 again (S105). In addition, the information processing device 310 (signal processing unit 311) may transmit, to the information processing device 230 on the first system 200 side through the predetermined network N1, information related to the above-described signal processing provided to the image data D111b (S103).

The following describes an exemplary procedure of processing on the first system 200 side. In the first system 200, the information processing device 230 (signal processing unit 232) provides various kinds of signal processing to the image data D111a corresponding to a result of image capturing of an object by the image capturing device 201 (S107). Then, the information processing device 230 (input-output control unit 233) presents an image based on the image data D111a provided with the signal processing to the operator 167 (in other words, an operating surgeon) performing manipulation on the surgery room side through the output device 204 (S109). The signal processing provided to the image data D111a by the information processing device 230 corresponds to exemplary "first signal processing".

The information processing device 230 (signal processing unit 232) may acquire, from the information processing device 310 on the second system 300 side, information related to image processing provided to the image data D111b on the second system 300 side. In this case, the information processing device 230 (signal processing unit 232) may provide, to the image data D111a, signal processing in accordance with the information acquired from the information processing device 310.

As described above, in the medical observation system according to Example 1, a copy of the image data D111 is forwarded from the first system 200 to the second system 300, and in each system, signal processing is individually provided to the image data D111 held in the system. Thus, for example, processing related to image production, a display view angle, and the timing of processing switching due to zoom or the like are independently controlled in each of the first system 200 and the second system 300. Accordingly, in the first system 200 on the surgery room side, signal processing can be independently provided to the image data D111 irrespective of processing executed in the second system 300 on the instruction room side, which leads to further reduction of frame delay. In addition, in the second system 300 on the instruction room side, as well, processing executed in the first system 200 on the surgery room side does not need to be taken into consideration, and thus, for example, signal processing with a larger processing load (in other words, a longer processing time) can be provided to the image data D111.

In addition, with a configuration as described above, processing related to display of an image corresponding to the image data D111 can be independently controlled in each of the first system 200 on the surgery room side and the second system 300 on the instruction room side. As a specific example, the image data D111 is generated in accordance with a result of image capturing of an object by the image capturing device 201 configured as a stereo camera. In such a case, a 3D image corresponding to the above-described image data D111 can be displayed in the first system 200 on the surgery room side, and a 2D image corresponding to the above-described image data D111 can be displayed in the second system 300 on the instruction room side.

It can be assumed that the environment in which a user views an image corresponding to the image data D111 is different between the surgery room and the instruction room. As a specific example, when fluorescence observation is performed, a situation in which the surgery room is dark is assumed, and an image corresponding to the image data D111 is generated on the assumption of image viewing in a dark room (in other words, image production is performed) in some cases. In such a case as well, the instruction room does not need to be made dark, and thus an image corresponding to the image data D111 can be generated (in other words, image production can be performed) on the assumption of a situation of image viewing in a bright room.

In addition, in the medical observation system according to the present embodiment, the first system 200 on the surgery room side and the second system 300 on the instruction room side can be individually established. Thus, for example, when an installation space is limited on the surgery room side and thus the number of installed display devices such as displays is restricted, a plurality of display devices (in other words, a multi-monitor configuration) can be used as long as sufficient space is obtained on the instruction room side. With this configuration, for example, when a special-light image, a normal-light image, and a superimposed image are selectively displayed in a switching manner on the surgery room side in a situation in which special light observation is performed, the images can be simultaneously displayed by using multiple monitors on the instruction room side.

As described above, with the medical observation system according to the present embodiment, information related to signal processing provided to image data based on an instruction from the instructor 399 in the second system 300 on the instruction room side is forwarded to the first system 200 on the surgery room side. With such a configuration, the information processing device 230 on the first system 200 side can reproduce the signal processing provided to the image data based on the instruction from the instructor 399 on the second system 300 side. Thus, for example, when a point or the like is drawn on an operation field image by the instructor 399 on the instruction room side, the information processing device 230 can reproduce, in image data held by the information processing device 230, the drawing by the instructor 399.

Figure 6:
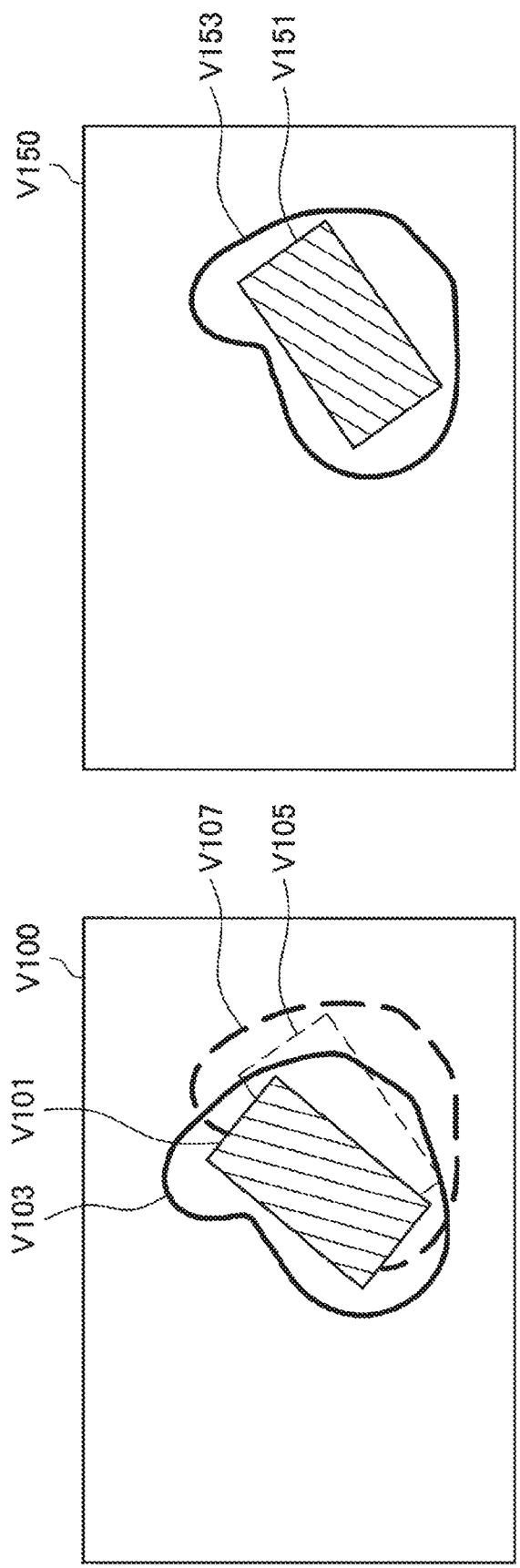
FIG. 6 is an explanatory diagram for describing exemplary signal processing provided to image data by the medical observation system according to Example 1.

For example, FIG. 6 is an explanatory diagram for describing exemplary signal processing provided to image data by the medical observation system according to Example 1. In FIG. 6, an image V100 indicates an exemplary image displayed on the output device 204 (in other words, an image presented to the operator 167) based on the image data D111a in the first system 200 on the surgery room side. In addition, an image V150 indicates an exemplary image displayed on the output device 330 (in other words, an image presented to the instructor 399) based on the image data D111b in the second system 300 on the instruction room side. In addition, in FIG. 6, Reference sign V101 schematically indicates an object image (for example, an image of an affected part) captured in the image V100. Similarly, Reference sign V151 schematically indicates the object image captured in the image V150.

In the example illustrated in FIG. 6, a mark (hereinafter also referred to as "instruction data V153") enclosing the object image V151 is drawn in the image V150 presented to the instructor 399 on the instruction room side, based on an instruction from the instructor 399. Through such processing, the instruction data V153 drawn in the image V150 presented on the instruction room side is reflected on the image V100 presented to the operator 167 on the surgery room side.

However, delay (what is called frame delay) sometimes occurs between the image V100 displayed on the surgery room side and the image V150 displayed on the instruction room side due to image data forwarding, difference in signal processing provided to each image, and the like. Thus, when providing signal processing related to presentation of the instruction data V153 to the image data D111a, the information processing device 230 on the first system 200 side may correct the shape and presented position of the instruction data V153 with the delay taken into account. For example, Reference sign V103 indicates instruction data presented with the delay taken into account and corresponds to the instruction data V153. Reference sign V105 schematically indicates the position and shape of the object image V151 presented in the image V150. Reference sign V107 schematically indicates the position and shape of the instruction data V153 presented in the image V150.

When the instruction data V103 in accordance with an instruction from the instructor 399 on the instruction room side is presented in the image V100 presented on the surgery room side, the instruction data V103 may be presented in a presentation aspect (for example, color or line thickness) different from that of the instruction data V153. As a specific example, since the image V100 is viewed by the operator 167 on the surgery room side, the presentation aspect of the instruction data V103 may be controlled to an aspect that allows easy viewing on the surgery room side. In addition, the instruction data V103 and V153 are viewed by respective users (which are the operator 167 and the instructor 399) different from each other. Thus, the presentation aspect of at least one of the instruction data V103 and V153 may be controlled in accordance with a user associated with an image in which the instruction data is presented (in other words, a user as a presentation target of the image). As a specific example, when an aged doctor is assumed as the instructor 399, the presentation aspect of the instruction data V153 may be controlled to an aspect that allows easy viewing by the aged doctor.

Not only the presentation aspect of instruction data but also the presentation aspect of an image may be controlled in accordance with a user associated with the image (in other words, a user as a presentation target of the image).

The following describes, as a specific example, exemplary control of the presentation aspect of an image presented to the instructor 399 assumed to be an aged doctor. For example, the capability of identifying yellow tends to decrease with aging. In particular, yellow corresponds to the color of fat and the like, and a situation in which the identifiability thereof decreases is not preferable. Thus, a part of a color, the identifiability of which decreases with aging in an image presented to the instructor 399 may be provided with processing related to replacement with another color, processing of increasing difference in luminance and color difference, and the like to further improve the identifiability.

As another example, the capability of identifying a minute part such as a blood vessel or a nerve tends to decrease as eyesight decreases with aging. Thus, for example, an image presented to the instructor 399 may be provided with correction processing assuming influence of decreasing eyesight (in other words, processing of inversely correcting the decreasing eyesight), such as what is called enhancement processing.

The above description is made mainly with a focus on a case in which an image corresponding to a result of image capturing by the image capturing device 201 is presented to the operator 167 or the instructor 399. However, information presented to each user is not particularly limited to an image as long as the information is information based on medical data, such as in-surgery information, and for example, audio such as voice may be presented. As a specific example, it can be assumed that voice of the operator 167 collected on the surgery room side is presented to the instructor 399 on the instruction room side. In such a case, as well, for example, the presentation aspect of information based on voice data (audio data) based on a result of the voice collection may be independently controlled in each of the first system 200 on the surgery room side and the second system 300 on the instruction room side. As a specific example, in any of the first system 200 and the second system 300, the voice data may be converted into text information through voice recognition processing and natural language processing, and the text information may be presented to the corresponding user through a display device.

In addition, when voice (audio) is presented to a user, the presentation aspect of the voice may be controlled in accordance with the user as a presentation target of the voice. As a specific example, it can be assumed that, when voice (audio) is presented to an aged doctor (the instructor 399), the doctor has difficulties in hearing the voice due to decrease of hearing ability with aging. Thus, for example, the voice presented to the instructor 399 (who is the aged doctor) may be provided with audio processing that allows the instructor 399 to easily hear the voice, such as frequency control, pitch control, or vowel and consonant volume control.

As described above, with the medical observation system according to the present embodiment, the instructor 399 can instruct, in a more preferable aspect from a room (the instruction room) different from a surgery room, the operator 167 performing manipulation in the surgery room. In the instruction room (which is another room separated from the surgery room), the state of a patient does not need to be considered as much as in the surgery room, and operability in surgery does not need to be considered as well, and thus an environment (for example, air conditioning, illumination, and disposition of desks, chairs, and the like) in which, for example, the instructor 399 can comfortably and easily work can be more flexibly established. Thus, when the instructor 399 is an aged surgeon, a load (for example, a physical load) on the instructor 399 is reduced and, for example, physical problem of the aged surgeon is expected to be solved. In addition, since the instructor 399 does need to directly perform manipulation, a physical load on the instructor 399 is reduced, which is expected to contribute to improvement of judgement capacity.

The above description with reference to FIGS. 5 and 6 is made on, as Example 1, exemplary control for the instructor 399 to instruct, in a more preferable aspect from the outside of the surgery room (from the instruction room), the operator 167 performing manipulation on the surgery room side in a system configuration as illustrated in FIG. 3.

Example 2

The following describes, as Example 2, another aspect of the medical observation system according to Example 1 described above.

In a situation of surgery in which the medical observation system according to the present embodiment is applied, various kinds of information corresponding to a result of detection by the detection device 211 include information (data) monitored by an anesthesiologist, such as vital data of a patient, in some cases. Data monitored by another user, such as the anesthesiologist, different from the operator 167 and the instructor 399 may be provided with signal processing in accordance with an instruction from the user and then forwarded to the second system 300 on the instruction room side.

Figure 7:
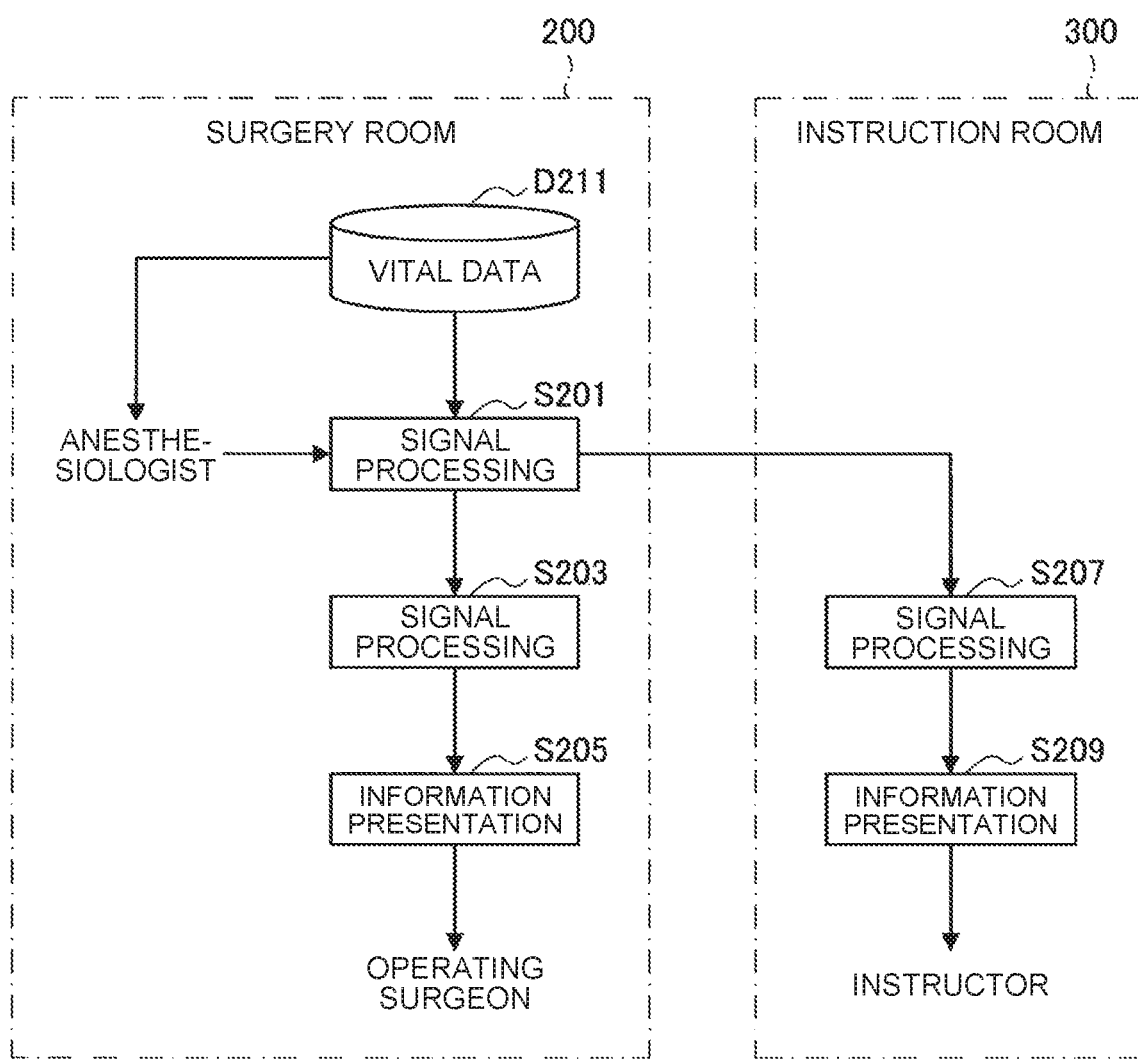
FIG. 7 is an explanatory diagram for describing an exemplary procedure of a series of processing at the medical observation system according to Example 2.

The following describes an exemplary procedure of a series of processing at the medical observation system according to Example 2 with reference to FIG. 7, with a focus on flow of information, in particular. FIG. 7 is an explanatory diagram for describing the exemplary procedure of a series of processing at the medical observation system according to Example 2.

The example illustrated in FIG. 7 indicates flow of information monitored by an anesthesiologist among various kinds of information acquired in surgery. With the example illustrated in FIG. 7, the following describes processing on vital data D211 of the patient acquired in surgery, assuming that the anesthesiologist is monitoring the vital data D211.

As illustrated in FIG. 7, the vital data D211 acquired in accordance with a result of detection by the detection device 211 is provided with signal processing in accordance with an instruction from the anesthesiologist by the information processing device 230 (signal processing unit 232) in the second system 300 on the surgery room side (S201). In the present embodiment, the anesthesiologist (in other words, a doctor different from the operator 167 and the instructor 399) corresponds to an exemplary "third user". The third user as a user on the first system 200 side may correspond to an exemplary "user associated with the first medical signal processing device". In addition, the above-described signal processing in accordance with an instruction from the anesthesiologist corresponds to exemplary "third signal processing" in the present embodiment.

Then, the vital data D211 provided with the signal processing is forwarded from the first system 200 on the surgery room side to the second system 300 on the instruction room side through the predetermined network N1. In this case, a copy of the vital data D211 provided with the signal processing in accordance with an instruction from the anesthesiologist in the first system 200 is forwarded to the second system 300. Accordingly, the vital data D211 is held in each of the first system 200 and the second system 300. Thus, in the following description, for sake of simplicity, the vital data D211 before being provided with the signal processing in accordance with an instruction from the anesthesiologist is also referred to as "vital data D211$a$" and distinguished from the vital data D211 provided with the signal processing. In addition, as for the vital data D211 provided with the signal processing, the vital data D211 held on the first system 200 side is also referred to as "vital data D211$b$", and the vital data D211 held on the second system 300 side (in other words, the vital data D211 forwarded to the second system 300) is also referred to as "vital data D211$c$". When not distinguished one from another, in particular, the vital data D211$a$, D211$b$, and D211$c$ are simply referred to as the "vital data D211". The vital data D211$b$ corresponds to exemplary "first information" in the present example. The vital data D211$c$ corresponds to exemplary "second information" in the present example.

Then, the information processing device 230 (signal processing unit 232) may additionally provide signal processing to the vital data D211$b$ provided with the signal processing in accordance with an instruction from the anesthesiologist (S203). Then, the information processing device 230 (input-output control unit 233) presents information based on the vital data D211$b$ provided with the signal processing to the operator 167 (in other words, the operating surgeon) performing manipulation on the surgery room side through the output device 204 (S205). The above-described signal processing provided to the vital data D211$b$ corresponds to exemplary "fourth signal processing" in the present example.

The following describes an exemplary procedure of processing on the second system 300 side. In the second system 300, the information processing device 310 (signal processing unit 311) provides various kinds of signal processing to the vital data D211$c$ forwarded from the information processing device 230 on the first system 200 side (S207). Then, the information processing device 310 (input-output control unit 313) presents information based on the vital data D211$c$ provided with the signal processing to the user (instructor 399) on the instruction room side through the output device 330 (S105). The above-described signal processing provided to the vital data D211$c$ corresponds to exemplary "fifth signal processing" in the present example.

As described above, when various kinds of information are forwarded from the first system 200 to the second system 300, signal processing common to the first system 200 and the second system 300 may be provided to target information before being forwarded.

In addition, as described above, in the medical observation system according to Example 2, a copy (which is the vital data D211$c$) of the vital data D211 provided with the signal processing in accordance with an instruction from the anesthesiologist is forwarded from the first system 200 to the second system 300. Accordingly, the vital data D211 provided with the signal processing in accordance with an instruction from the anesthesiologist is individually held in each of the first system 200 and the second system 300.

Thus, in each system, signal processing can be individually provided to the vital data D211 held in the system.

In addition, presentation of information corresponding to the vital data D211 can be individually controlled in each of the first system 200 and the second system 300. Thus, for example, the type and amount of information presented to each of the operator 167 (operating surgeon) on the surgery room side and the instructor 399 on the instruction room side can be individually controlled. As a specific example, such control can be performed in which all information corresponding to the vital data D211 is presented to one user among the operator 167 and the instructor 399 and only part of the information corresponding to the vital data D211 is presented to the other user. More specifically, all information corresponding to the vital data D211 may be presented to the instructor 399 on the instruction room side since multiple monitors can be used. However, only part of the information corresponding to the vital data D211 may be presented as a ticker or the like to the operator 167 on the surgery room side since the number of display devices that can be used is limited.

The above description with reference to FIG. 7 is made on, as Example 2, another aspect of the above-described medical observation system according to Example 1.

Example 3

The following describes, as Example 3, an exemplary technology with which the operator 167 on the surgery room side and the instructor 399 on the instruction room side can cooperate with each other in a more preferable aspect in the progress of surgery.

Figure 8:
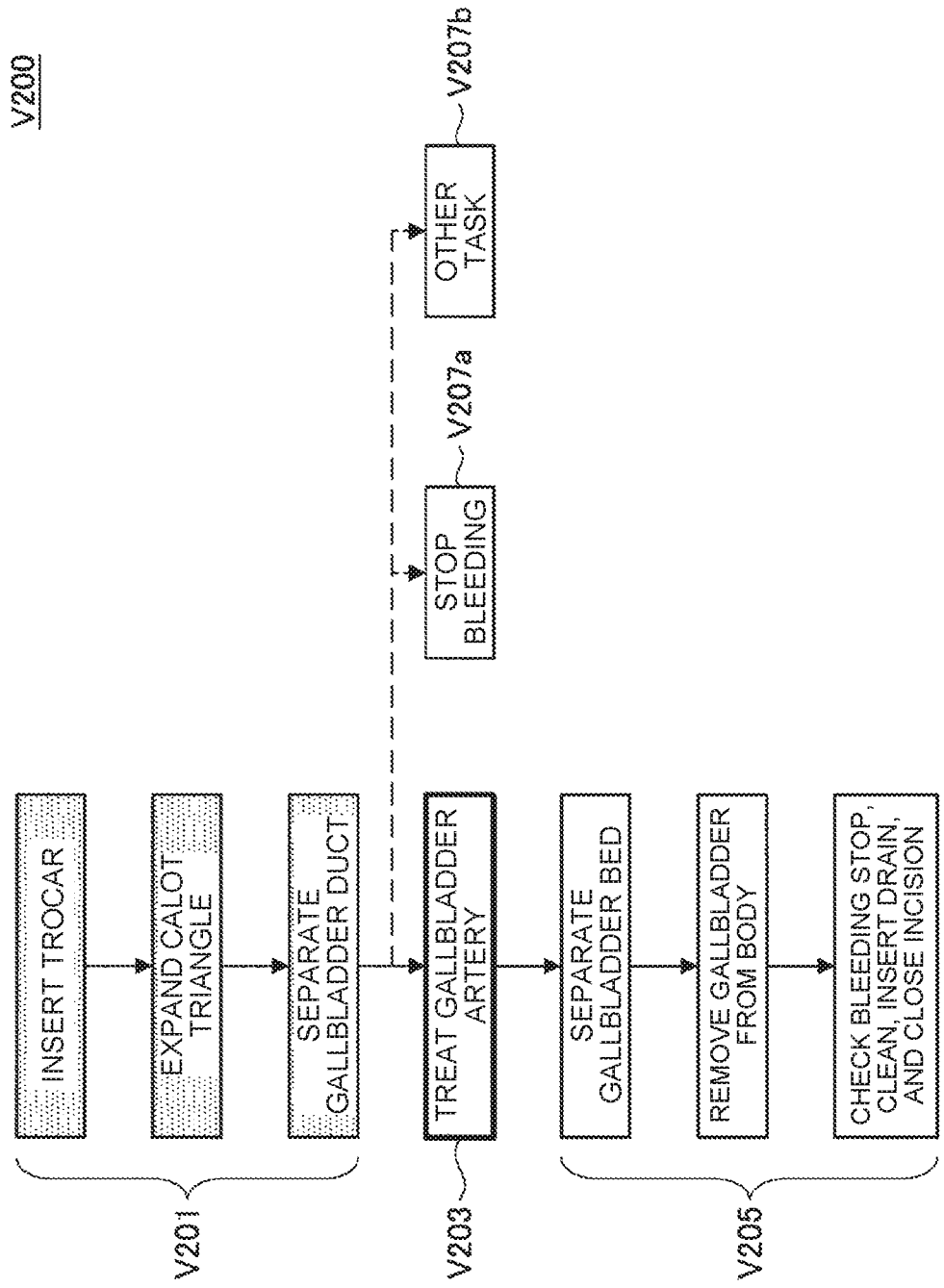
FIG. 8 is a diagram illustrating an exemplary surgical procedure presented to an operator and an instructor in the medical observation system according to Example 3.

Specifically, in a medical observation system according to the present example, display information (hereinafter also referred to as a "surgical procedure V200") indicating the procedure of surgery to be performed is presented to each of the operator 167 on the surgery room side and the instructor 399 on the instruction room side through a display device. For example, FIG. 8 is a diagram illustrating an exemplary surgical procedure V200 presented to each of the operator and the instructor in the medical observation system according to Example 3, and illustrates an exemplary procedure of surgery to remove gallbladder.

The surgical procedure V200 is generated based on, for example, surgery information registered in a database or the like. In addition, the generated surgical procedure V200 is displayed to the first system 200 and the second system 300 in common. As a specific example, information for displaying the generated surgical procedure V200 on a display device as display information is directly or indirectly shared between the first system 200 and the second system 300, and when the surgical procedure V200 is updated in one of the systems, the update is reflected on the other system.

In the surgical procedure V200, steps of the corresponding surgery (in other words, tasks performed in the surgery) are presented as a list in a temporally sequential manner. For example, in the example illustrated in FIG. 8, steps of the surgery to remove gallbladder are presented as a list in a temporally sequential manner downward. In addition, in the surgical procedure V200, a step performed, a step being performed, and a step to be performed (step scheduled to be performed) are presented in an identifiable manner with different display aspects such as colors. In the example illustrated in FIG. 8, Reference signs V201, V203, and V205 indicate performed steps, a step being performed, and steps to be performed, respectively.

For example, the situation of the surgery may be determined in accordance with various kinds of information acquired in the first system 200 on the surgery room side, and the progress of the surgical procedure V200 may be updated in accordance with a result of the determination. As a specific example, whether a step being performed in the surgical procedure V200 is completed may be determined in accordance with a result of analysis of an image of the operation place or the operation field, which is captured by the image capturing device 201, and the progress of the surgical procedure V200 may be updated in accordance with a result of the determination.

As another example, the progress of the surgical procedure V200 may be updated in accordance with a result of recognition of voice related to an instruction spoken by the operator 167 or the instructor 399. As a specific example, when the operator 167 instructs a nurse or the like assisting the surgery to prepare a device or a surgical instrument for performing predetermined treatment, a step to be subsequently performed can be estimated by recognizing voice related to the instruction. When an explicit instruction related to update of the progress of the surgical procedure V200 is spoken by the operator 167 or the instructor 399, the progress of the surgical procedure V200 may be updated in accordance with a result of recognition of voice related to the instruction.

The above-described example is merely exemplary. Thus, as long as the surgical procedure V200 can be updated along with the actual progress of the surgery by recognizing whether a step being performed is completed, which step is being performed, or the like in accordance with results of recognition of various states and situations, the method of the update is not particularly limited. Alternatively, the progress of the surgical procedure V200 may be updated in accordance with an instruction from the operator 167 or the instructor 399 through an input device.

The next step (for example, treatment to be subsequently performed) potentially changes in accordance with the situation of the surgery. Thus, the surgical procedure V200 may present a plurality of candidates as steps to be subsequently performed. For example, in the example illustrated in FIG. 8, step V207a of "stop bleeding" is presented in addition to step V203 of "gallbladder artery treatment". In addition, step V207b of a task, which is indicated as "other task", other than "gallbladder artery treatment" and "stop bleeding" may be presented.

In addition, update of at least some of the steps of the surgical procedure V200, addition of a candidate for a step to be subsequently performed, or the like may be performed in accordance with an instruction from at least one of the operator 167 and the instructor 399. With such a configuration, for example, the instructor 399 can update the surgical procedure V200 in real time while checking the progress of the surgery and thus can instruct, in accordance with the current situation, a task to be subsequently performed to the operator 167 performing manipulation in the surgery room.

With the medical observation system according to Example 3 having the above-described configuration, the operator 167 on the surgery room side and the instructor 399 on the instruction room side can refer to the surgical procedure V200 common to the operator 167 and the instructor 399 to share recognition of the progress of the surgery or the next task. Thus, with the medical observation system according to Example 3, the operator 167 and the instructor 399 can proceed the surgery while cooperating with each other in a more preferable aspect.

The above description with reference to FIG. 8 is made on, as Example 3, an exemplary technology with which the operator 167 on the surgery room side and the instructor 399 on the instruction room side can cooperate with each other in a more preferable aspect in the progress of surgery.

Example 4

The following describes, as Example 4, more specific exemplary arrangement for achieving the medical observation system according to the present embodiment described above, with a focus on information transmission and reception between the first system 200 on the surgery room side and the second system 300 on the instruction room side, in particular.

As described above, in the medical observation system according to the present embodiment, the operator 167 (operating surgeon) and the instructor 399 in rooms different from each other (in other words, spaces isolated from each other) view various kinds of information (for example, an image captured by the image capturing device 201) acquired on the surgery room side. A configuration for achieving such a use case is, for example, a configuration in which an image actually displayed on a display device on the surgery room side is forwarded from the first system 200 on the surgery room side to the second system 300 on the instruction room side. However, in this case, an image provided with various kinds of signal processing for display on the display device in the first system 200 is forwarded to the second system 300, and thus signal processing applicable to the image in the second system 300 is limited in some cases.

As a specific example, when enlarged display is performed in the first system 200, an image after the enlargement processing is forwarded to the second system 300. Thus, for example, it is potentially difficult to present a part excluded as a display target through the enlargement processing (in other words, a part different from an enlarged part) to the instructor 399 on the instruction room side. In particular, when an image at high resolution such as 8 K is captured, an image of a patient is captured at a wider view angle, and then a part of interest is cut out and displayed in some cases. In such a situation, when the cut-out image is forwarded from the first system 200 to the second system 300, it is difficult to restore a part different from the cut-out part and present the part to the instructor 399 on the second system 300 side.

In the medical observation system according to the present embodiment, the operator 167 (operating surgeon) actually performing manipulation in the surgery room and the instructor 399 instructing the operator 167 from the instruction room cooperatively proceed surgery. With such a situation, arrangement is desired that can reduce delay (for example, frame delay at image display) between the first system 200 on the surgery room side and the second system 300 on the instruction room side as much as possible.

With a situation as described above, the present example discloses more detailed exemplary arrangement with which the first system 200 and the second system 300 can each more flexibly apply signal processing to a result of image capturing of an object (for example, the operation place or the operation field) and the amount of communication between the systems is optimized (for example, further limited).

Figure 9:
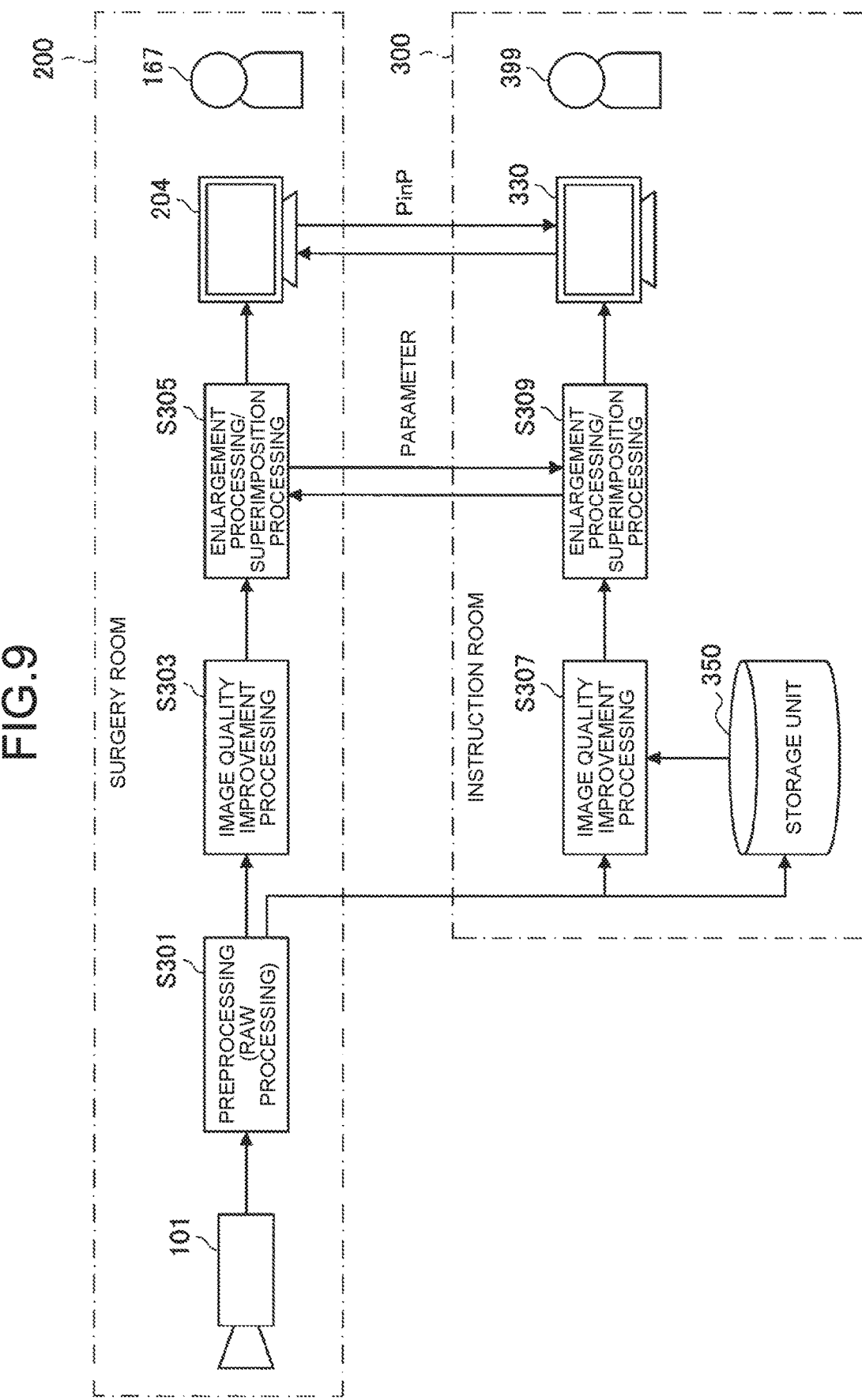
FIG. 9 is an explanatory diagram for describing an exemplary procedure of processing at the medical observation system according to Example 4.

FIG. 9 is an explanatory diagram for describing an exemplary procedure of processing at a medical observation system according to Example 4. In the example illustrated in FIG. 9, the medical observation system includes the first system 200 on the surgery room side and the second system 300 on the instruction room side, which are connected through the network N1, as described with reference to FIGS. 3 and 4.

As illustrated in FIG. 9, in the first system 200 on the surgery room side, RAW data (image data) is acquired in accordance with a result of image capturing of an object by the image capturing device 201 (medical observation device) and provided with minimum signal processing (RAW processing) such as defect pixel correction (S301). In this case, the RAW data may be provided with signal processing other than RAW processing. The minimum signal processing (RAW processing) provided to the RAW data corresponds to exemplary "third signal processing" in the present example.

A copy of the RAW data provided with the RAW processing is forwarded to the second system 300 on the instruction room side so that the RAW data is independently held in each of the first system 200 and the second system 300. Thus, in the following description, the RAW data provided with the RAW processing held on the first system 200 side is also referred to as "image data D311a", and the RAW data provided with the RAW processing held on the second system 300 side is also referred to as "image data D311b". When not distinguished from each other, in particular, the image data D311a and D311b are simply referred to as "image data D311".

Information acquired on the first system 200 side is not limited to RAW data corresponding to a result of image capturing by the image capturing device 201. For example, various states (for example, the state of the patient and the state of the surgery room) may be detected by the detection device 211 (for example, a sensor), and information corresponding to a result of the detection may be acquired. In addition, audio in the surgery room, voice of the operator 167, and the like may be collected by the sound collection device 203, and audio data and voice data corresponding to a result of the collection may be acquired. A copy of such information (data) other than RAW data acquired on the first system 200 side may be forwarded from the first system 200 to the second system 300. Thus, in the medical observation system according to the present example, medical data such as the above-described in-surgery information can be a processing target in a manner substantially same as that for the above-described image data D311 except for difference in the data type. This is same for various kinds of processing described later.

Then, in the first system 200 on the surgery room side, various kinds of signal processing such as image quality improvement processing (S303) and enlargement processing/superimposition processing (S305) are provided to the image data D311a held on the first system 200 side. Then, an image corresponding to the image data D311a provided with the various kinds of signal processing (S303 and S305) is presented to the operator 167 through the output device 204. The various kinds of signal processing such as the image quality improvement processing (S303) and the enlargement processing/superimposition processing (S305) provided to the image data D311a correspond to exemplary "first signal processing" in the present example. The image data D311a provided with the first signal processing corresponds to exemplary "second image data" in the present example. Image data to be forwarded to the second system 300 on the instruction room side, in other words, the image data D311a before being provided with the first signal processing and the image data D311b held in the second system 300 correspond to exemplary "first image data" in the present example.

In the second system 300 on the instruction room side, various kinds of signal processing such as image quality improvement processing (S307) and enlargement processing/superimposition processing (S309) are provided to the image data D311b forwarded from the first system 200. Then, an image corresponding to the image data D311a provided with the various kinds of signal processing (S307 and S309) is presented to the instructor 399 through the output device 330. The various kinds of signal processing such as the image quality improvement processing (S307) and the enlargement processing/superimposition processing (S309) provided to the image data D311b correspond to exemplary "second signal processing" in the present example.

The set of various kinds of signal processing (S303 and S305) provided to the image data D311a in the first system 200 and the set of various kinds of signal processing (S307 and S309) provided to the image data D311b in the second system 300 can be executed independently from each other. Thus, pieces of signal processing different from each other can be provided to the image data D311 in the first system 200 and the second system 300, respectively. As a specific example, in the first system 200 on the surgery room side, signal processing provided to the image data D311a may be limited to further reduce delay. In the second system 300 on the instruction room side, since multiple monitors can be used, a plurality of images may be generated by individually providing a plurality of kinds of signal processing to the image data D311b to display images different from each other on a plurality of respective display devices.

The timing at which various kinds of signal processing are provided to the image data D311 does not necessarily need to be synchronized between the first system 200 and the second system 300. Thus, for example, in the second system 300, the image data D311b forwarded from the first system 200 may be temporarily or permanently stored in a predetermined storage region (hereinafter referred to as "storage unit 350"). In this case, the image data D311b stored in the storage unit 350 may be provided with the above-described various kinds of signal processing such as the image quality improvement processing (S307) and the enlargement processing/superimposition processing (S309). The second system 300 may sequentially provide the above-described various kinds of signal processing to the image data D311b sequentially forwarded from the first system 200. With such a configuration, the second system 300 may execute signal processing on the sequentially forwarded image data D311b and presentation of an image corresponding to the image data D311b provided with the signal processing in real time.

In the medical observation system according to the present embodiment, it can be assumed that an image generated in one of the first system 200 and the second system 300 is presented on the other system side. In such a case, for example, when an image generated in each system (in other words, an image provided with signal processing) is transmitted and received between the systems, the amount of communication between the systems increases, and delay (frame delay) sometimes occurs between an image generated in one of the systems and an image forwarded from the other system.

Thus, in the medical observation system according to the present example, instead of an image generated in one of the first system 200 and the second system 300, information related to signal processing (for example, a parameter of the signal processing) applied to generate the image is transmitted to the other system. In this case, the other system reproduces the image generated in the one system by providing signal processing to image data held in the other system based on the information related to the signal processing and transmitted from the one system.

As a more specific example, when image enlargement processing provided in the one system is to be reproduced in the other system, for example, a parameter related to the view angle and set for the enlargement processing is preferably forwarded from the one system to the other system. Accordingly, the image enlargement processing provided in the one system can be reproduced in the other system by cutting out an image from the image data D311 held in the other system based on the parameter related to the view angle.

With such a configuration, the amount of communication between the first system 200 and the second system 300 can be limited as compared to a case in which the image is transmitted and received between the systems. Accordingly, in a situation in which an image generated in the one system is presented on the other system side, delay between the image generated in the one system and the image forwarded from the other system can be reduced. Thus, when images provided with signal processing in both systems, respectively, are simultaneously presented by using a method such as a picture-in-picture (PinP) method, the images can be presented with shorter delay.

In the example illustrated in FIG. 9, RAW data provided with the RAW processing (S301) is forwarded from the first system 200 to the second system 300, which does not necessarily limit the operation of the medical observation system according to the present example. As a specific example, the RAW data before being provided with the RAW processing may be forwarded from the first system 200 to the second system 300, and the RAW processing may be individually provided in each of the first system 200 and the second system 300. In this case, whether the RAW data before being provided with the RAW processing or the RAW data provided with the RAW processing is to be forwarded between the first system 200 and the second system 300 may be selectively determined in accordance with, for example, the communication amount in the forwarding of the RAW data. Specifically, when the communication amount in a case in which the RAW data before the RAW processing and information related to the RAW processing (for example, a parameter of the RAW processing) are forwarded is smaller than that in a case in which the RAW data provided with the RAW processing is forwarded, the RAW data before the RAW processing and the information related to the RAW processing may be forwarded.

The signal processing provided, before forwarding to the second system 300, to the RAW data corresponding to a result of image capturing of an object by the image capturing device 201 (medical observation device) is not limited to the RAW processing. For example, signal processing that is common to the first system 200 and the second system 300 and provided to the RAW data corresponding to the result of image capturing of an object by the image capturing device 201 may be provided on the first system 200 side before forwarding to the second system 300.

The type of signal processing provided to the image data D311 in each of the first system 200 on the surgery room side and the second system 300 on the instruction room side is not necessarily limited to that in the example illustrated in FIG. 9. As a specific example, signal processing such as color adjustment, adjustment of the depth of field, or adjustment (enhancement) of parallax in 3D display may be included. In addition, as another example, processing in which special light observation using indocyanine green (ICG) or the like and normal light observation (white light observation; white light imaging (WLI)) using visible light are selectively switched may be included, or signal processing in accordance with these observation methods may be included.

The above description is made on an exemplary procedure of processing at the medical observation system according to the present example with a focus on, when an image corresponding to a result of image capturing by the image capturing device 201 is displayed, information transmitted and received between the first system 200 and the second system 300 to display the image. However, the application target of the above-described series of processing is not limited to processing related to image display. As a specific example, the above-described series of processing is applicable when various kinds of signal processing are applied to voice data (audio data) corresponding to a result of sound collection by a sound collection device and information corresponding to a result of detection by a detection device (for example, various sensors). Similarly, the above-described series of processing is applicable except for difference in the data type when desired signal processing is applied to medical data such as the above-described in-surgery information.

With the medical observation system according to the present example having the above-described configuration, the first system 200 and the second system 300 can apply, independently from each other, signal processing on image data (RAW data) corresponding to a result of image capturing by the image capturing device 201. Thus, the first system 200 and the second system 300 can each more flexibly apply signal processing to a result of image capturing of an object (for example, the operation place or the operation field).

In addition, in the medical observation system according to the present example, when an image generated in one of the first system 200 and the second system 300 is to be presented in the other system, information related to signal processing (for example, a parameter of the signal processing) applied in the one system is transmitted to the other system. Then, the other system reproduces the image generated in the one system by providing signal processing to image data held in the other system based on the above-described information related to the signal processing and transmitted from the one system. With the medical observation system according to the present example having such a configuration, the amount of communication between the systems can be limited as compared to a case in which the image is transmitted and received between the systems. Thus, for example, in a situation in which an image generated in the one system is presented on the other system side, delay between the image generated in the one system and an image forwarded from the other system can be reduced.

The above description with reference to FIG. 9 is made on, as Example 4, more specific exemplary arrangement for achieving the above-described medical observation system according to the present embodiment, with a focus on information transmission and reception between the first system 200 on the surgery room side and the second system 300 on the instruction room side, in particular.

4. EXEMPLARY HARDWARE CONFIGURATION

Figure 10:
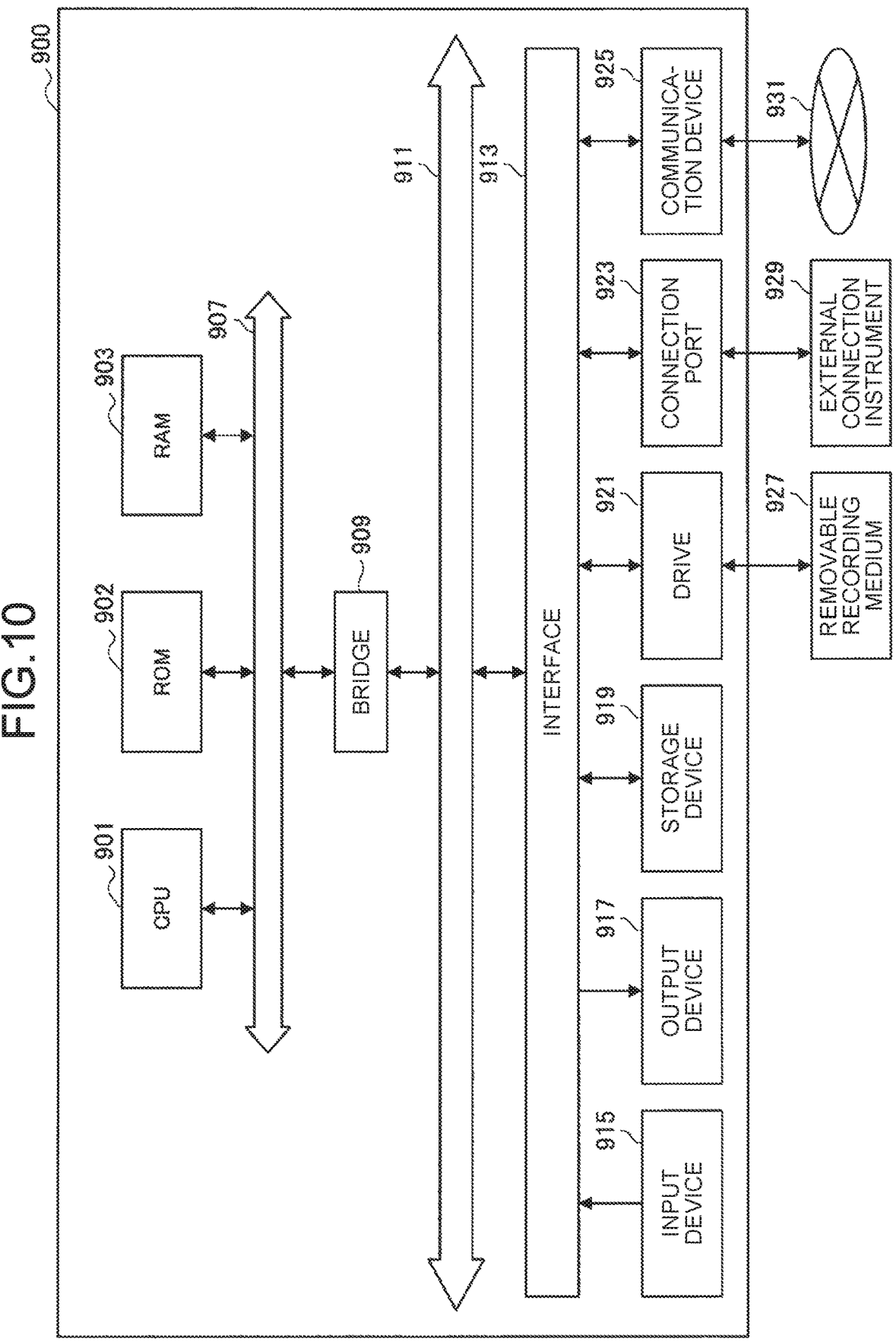
FIG. 10 is a functional block diagram illustrating an exemplary hardware configuration of an information processing device included in the medical observation system according to an embodiment of the present disclosure.

The following describes an exemplary hardware configuration of an information processing device (for example, the information processing devices 230 and 310 illustrated in FIG. 3) configured to execute various kinds of processing in the medical observation system according to the present embodiment in detail with reference to FIG. 10. FIG. 10 is a functional block diagram illustrating an exemplary hardware configuration of an information processing device included in an endoscope image capturing system according to an embodiment of the present disclosure.

This information processing device 900 included in the endoscope image capturing system according to the present embodiment mainly includes a CPU 901, a ROM 903, and a RAM 905. In addition, the information processing device 900 includes a host bus 907, a bridge 909, an external bus 911, an interface 913, an input device 915, an output device 917, a storage device 919, a drive 921, a connection port 923, and a communication device 925.

The CPU 901 functions as an arithmetic processing device and a control device and entirely or partially controls the operation of the information processing device 900 in accordance with various computer programs recorded in the ROM 903, the RAM 905, the storage device 919, or a removable recording medium 927. The ROM 903 stores a computer program used by the CPU 901, a calculation parameter, and the like. The RAM 905 primarily stores a computer program used by the CPU 901, a parameter that changes as appropriate in execution of the computer program, and the like. These are connected with each other through the host bus 907 formed by an internal bus such as a CPU bus. In the information processing device 230 illustrated in FIG. 4, the forwarding processing unit 231, the signal processing unit 232, the input-output control unit 233, and the device control unit 234 may be achieved by the CPU 901. Similarly, in the information processing device 310 illustrated in FIG. 4, the signal processing unit 311, the input-output control unit 313, and the remote control unit 315 may be achieved by the CPU 901.

The host bus 907 is connected with the external bus 911 such as a peripheral component interconnect/interface (PCI) bus through the bridge 909. The external bus 911 is connected with the input device 915, the output device 917, the storage device 919, the drive 921, the connection port 923 and the communication device 925 through the interface 913.

The input device 915 is an operation unit operated by a user, such as a mouse, a keyboard, a touch panel, a button, a switch, a lever, or a pedal. The input device 915 may be, for example, a remote control unit (what is called a remote controller) that uses infrared or other radio wave, or an external connection instrument 929 such as a cellular phone or a PDA corresponding to the operation of the information processing device 900. The input device 915 includes, for example, an input control circuit configured to generate an input signal based on information input by the user by using the above-described operation unit and configured to output the input signal to the CPU 901. The user of the information processing device 900 can input various kinds of data or instruct processing operation to the information processing device 900 by operating the input device 915. The input device 202 and the input device 320 illustrated in FIG. 4 may be achieved by the input device 915.

The output device 917 includes a device capable of visually or audibly notifying the user of acquired information. Examples of such devices include display devices such as a CRT display device, a liquid crystal display device, a plasma display device, an EL display device, and a lamp, sound output devices such as a speaker and headphones, and a printer device. For example, the output device 917 outputs a result obtained through various kinds of processing performed by the information processing device 900. Specifically, a display device displays, in text or image, the result obtained through various kinds of processing performed by the information processing device 900. A sound output device converts an audio signal made of regenerated voice data, audio data, or the like into an analog signal and outputs the analog signal. The output device 204 and the output device 330 illustrated in FIG. 4 may be achieved by the output device 917.

The storage device 919 is a data storage device configured as an exemplary storage unit of the information processing device 900. The storage device 919 includes, for example, a magnetic storage unit device such as a hard disk drive (HDD), a semiconductor storage device, an optical storage device, or a magneto-optical storage device. The storage device 919 stores a computer program executed by the CPU 901, various kinds of data, and the like.

The drive 921 is a recording-medium reader-writer built in or externally connected with the information processing device 900. The drive 921 reads information recorded on the removable recording medium 927 mounted thereon, such as a magnetic disk, an optical disk, a magneto optical disc, or a semiconductor memory, and outputs the information to the RAM 905. The drive 921 can write a record to the removable recording medium 927 mounted thereon, such as a magnetic disk, an optical disk, a magneto optical disc, or a semiconductor memory. The removable recording medium 927 is, for example, a DVD media, an HD-DVD media, or a Blu-ray (registered trademark) media. Alternatively, the removable recording medium 927 may be a CompactFlash (registered trademark) (CF), a flash memory, a Secure Digital memory card (SD memory card), or the like. Alternatively, the removable recording medium 927 may be, for example, an integrated circuit card (IC card) on which a non-contact IC chip is mounted or an electronic device.

The connection port 923 is a port for direct connection with the information processing device 900. Examples of the connection port 923 include a Universal Serial Bus (USB) port, an IEEE1394 port, and a Small Computer System Interface (SCSI) port. Other examples of the connection port 923 include an RS-232C port, an optical audio terminal, and a high-definition multimedia interface (registered trademark) (HDMI) port. When the external connection instrument 929 is connected with the connection port 923, the information processing device 900 directly acquires various kinds of data from the external connection instrument 929 and provides various kinds of data to the external connection instrument 929.

The communication device 925 is, for example, a communication interface including a communication device for connection with a communication network (network) 931. The communication device 925 is, for example, a communication card for a wired or wireless local area network (LAN), Bluetooth (registered trademark), or wireless USB (WUSB). Alternatively, the communication device 925 may be, for example, an optical communication router, an asymmetric digital subscriber line (ADSL) router, or various communication modems. For example, the communication device 925 can transmit and receive signals or the like to and from the Internet or another communication instrument according to a predetermined protocol such as TCP/IP. The communication network 931 connected with the communication device 925 may include a network or the like connected in a wired or wireless manner and may be, for example, the Internet, an in-home LAN, infrared communication, radio wave communication, or satellite communication. The communication unit 239 and the communication unit 319 illustrated in FIG. 4 may be achieved by the communication device 925.

The above description is made on an exemplary hardware configuration that can achieve functions of the information processing device 900 included in the endoscope image capturing system according to an embodiment of the present disclosure. Each above-described component may be achieved by using a general-purpose member or may be achieved by hardware specialized for the function of the component. Thus, a hardware configuration to be used can be changed as appropriate in accordance with a technology level when the present embodiment is performed. Although not illustrated in FIG. 10, it is clear that various components corresponding to the information processing device 900 included in the endoscope image capturing system are included.

A computer program for achieving each function of the information processing device 900 included in the endoscope image capturing system according to the present embodiment as described above can be produced and installed on a personal computer or the like. In addition, a computer-readable recording medium storing such a computer program can be provided. The recording medium is, for example, a magnetic disk, an optical disk, a magneto optical disc, or a flash memory. Alternatively, the above-described computer program may be distributed, for example, through a network without using the recording medium. In addition, the number of computers that execute the computer program is not particularly limited. For example, the computer program may be cooperatively executed by a plurality of computers (for example, a plurality of servers).

5. EXEMPLARY APPLICATION

Figure 11:
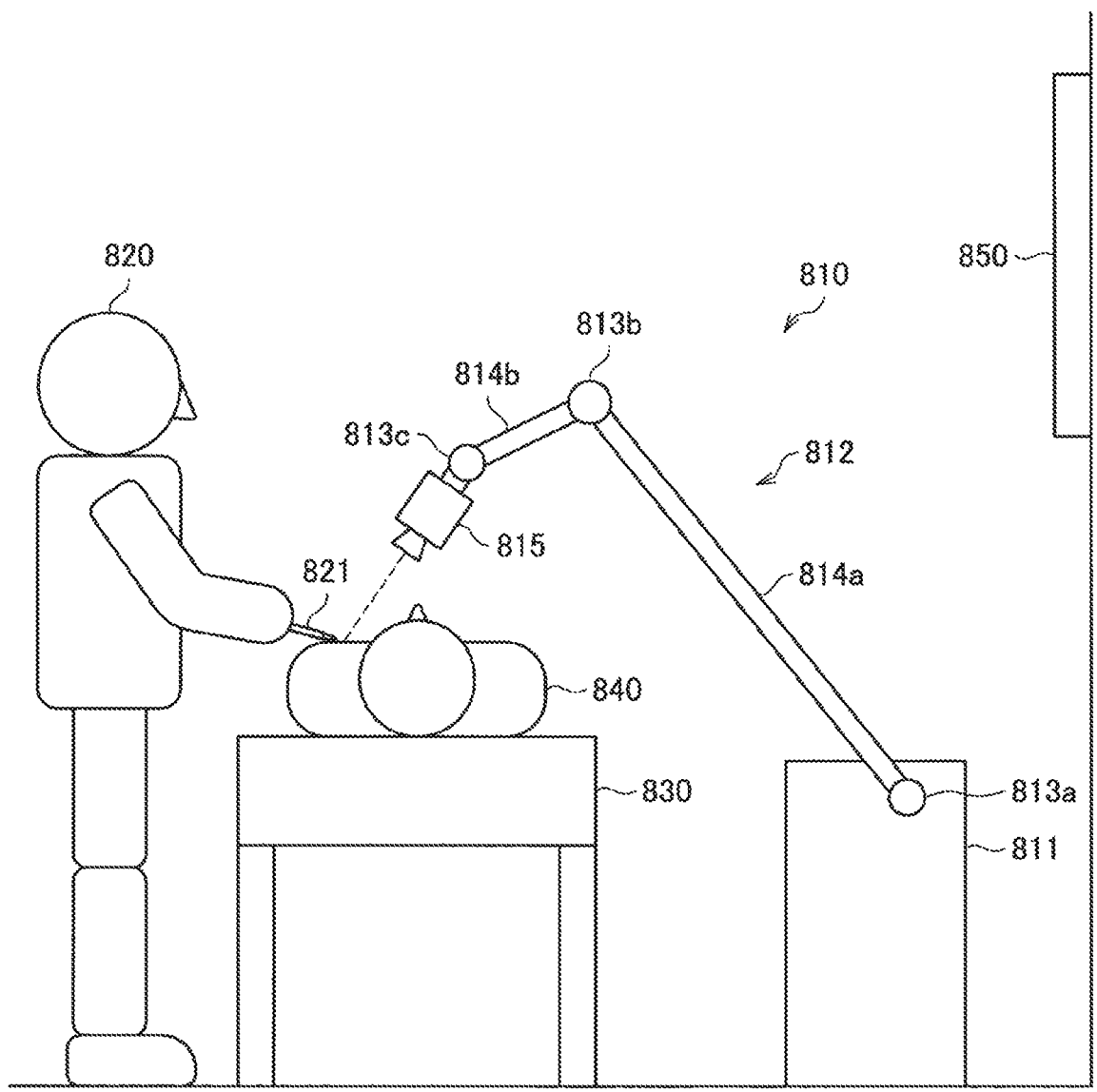
FIG. 11 is an explanatory diagram for describing an exemplary application of the medical observation system according to an embodiment of the present disclosure.

The following describes, as an exemplary application of the medical observation system according to an embodiment of the present disclosure, an exemplary case in which the medical observation system is configured as a microscope image capturing system including a microscope unit with reference to FIG. 11.

FIG. 11 is an explanatory diagram for describing the exemplary application of the medical observation system according to an embodiment of the present disclosure, illustrating an exemplary schematic configuration of the microscope image capturing system. Specifically, FIG. 11 illustrates, as an exemplary application when the microscope image capturing system according to an embodiment of the present disclosure is used, an exemplary case in which a surgical video microscope device including an arm is used.

For example, FIG. 11 schematically illustrates the status of a medical operation using the surgical video microscope device. Specifically, FIG. 11 illustrates a status in which a doctor as a practitioner (user) 820 performs surgery on an operation target (patient) 840 on an operation table 830 by using a surgical instrument 821 such as a scalpel, tweezers, or forceps. In the following description, a medical operation collectively means various medical treatments, such as surgery and examination, performed on a patient as the operation target 840 by the doctor as the user 820. Although the example of FIG. 11 illustrates the status of surgery as an exemplary medical operation, a medical operation in which this surgical video microscope device 810 is used is not limited to surgery but may be other various medical operations.

The surgical video microscope device 810 is provided beside the operation table 830. The surgical video microscope device 810 includes a base unit 811 as a base, an arm unit 812 extending from the base unit 811, and an image capturing unit 815 connected as a leading end unit at a leading end of the arm unit 812. The arm unit 812 includes a plurality of joint parts 813a, 813b, and 813c, a plurality of links 814a and 814b coupled with each other through the joint parts 813a and 813b, and the image capturing unit 815 provided at the leading end of the arm unit 812. In the example illustrated in FIG. 11, for simplification, the arm unit 812 includes the three joint parts 813a to 813c and the two links 814a and 814b, but in reality, while taking into account the degrees of freedom of the arm unit 812 and the image capturing unit 815 in position and posture, the numbers and shapes of the joint parts 813a to 813c and the links 814a and 814b, the directions of drive shafts of the joint parts 813a to 813c, and the like may be set as appropriate to achieve desired degrees of freedom.

The joint parts 813a to 813c have a function to couple the links 814a and 814b to be rotatable relative to each other, and drive of the arm unit 812 is controlled when rotation of the joint parts 813a to 813c is driven. In the following description, the position of each component of the surgical video microscope device 810 means a position (coordinates) in a space defined for drive control, and the posture of each component means an orientation (angle) relative to an optional axis in the space defined for drive control. In addition, in the following description, drive (or drive control) of the arm unit 812 means (control of) change of the position and posture of each component of the arm unit 812 through drive (or drive control) of the joint parts 813a to 813c and drive (or drive control) of the joint parts 813a to 813c.

The image capturing unit 815 as the leading end unit is connected with the leading end of the arm unit 812. The image capturing unit 815 is a unit that acquires an image of an image capturing object and is, for example, a camera capable of capturing a moving image or a still image. As illustrated in FIG. 11, the postures and positions of the arm unit 812 and the image capturing unit 815 are controlled by the surgical video microscope device 810 so that the image capturing unit 815 provided at the leading end of the arm unit 812 captures an image of the status of an operation site of the operation target 840. The configuration of the image capturing unit 815 connected as the leading end unit with the leading end of the arm unit 812 is not particularly limited and, for example, the image capturing unit 815 is configured as a microscope configured to acquire an enlarged image of the image capturing object. In addition, the image capturing unit 815 may be detachable from the arm unit 812. With such a configuration, for example, the image capturing unit 815 suits for a usage application may be connected as the leading end unit with the leading end of the arm unit 812 as appropriate. For example, an image capturing device to which a bifurcating optical system according to the above-described embodiment is applied may be applied as the image capturing unit 815. Thus, in the present exemplary application, the image capturing unit 815 or the surgical video microscope device 810 including the image capturing unit 815 may correspond to an exemplary "medical observation device". The present description is made with a focus on a case in which the image capturing unit 815 is applied as the leading end unit, but the leading end unit connected with the leading end of the arm unit 812 is not necessarily limited to the image capturing unit 815.

In addition, a display device 850 such as a monitor or a display is installed at a position facing the user 820. The image of the operation site captured by the image capturing unit 815 is displayed as an electronic image on a display screen of the display device 850. The user 820 performs various treatments while viewing the electronic image of the operation site displayed on the display screen of the display device 850.

With the above-described configuration, surgery can be performed while image capturing of an operation site is performed by the surgical video microscope device 810.

6. CONCLUSION

Preferable embodiments of the present disclosure are described above in detail with reference to the accompanying drawings, but the technical scope of the present disclosure is not limited to such examples. Various changes and modifications could be thought of by a person having typical knowledge in the technical field of the present disclosure within the range of the technical idea described in the claims, and it should be understood that these changes and modifications belong to the technical scope of the present disclosure.

Effects stated in the present specification are explanatory or exemplary but not restrictive. Thus, the technology according to the present disclosure achieves, together with or in place of the above-described effects, any other effect that is obvious to the skilled person in the art from description of the present specification.

Configurations as described below belong to the technical scope of the present disclosure.

(1)

A medical observation system comprising:

a first medical signal processing device including a first signal processing unit configured to acquire first image data corresponding to a result of image capturing of an affected part by a medical observation device and provide first signal processing to the first image data; and a second medical signal processing device including a second signal processing unit configured to acquire second image data corresponding to the result of image capturing from the first medical signal processing device through a predetermined network and provide second signal processing to the second image data, wherein the second signal processing unit transmits information related to the second signal processing to the first medical signal processing device, and the first signal processing unit controls the first signal processing in accordance with the second signal processing.

(2)

The medical observation system according to (1), wherein the second signal processing unit controls the second signal processing in accordance with information input from a user associated with the second medical signal processing device through a predetermined input unit, and transmits the information related to the second signal processing in accordance with a result of the control to the first medical signal processing device.

(3)

The medical observation system according to (2), wherein the predetermined input unit is disposed in a room different from a room in which the medical observation device is disposed.

(4)

The medical observation system according to (2) or (3), further comprising a control unit configured to control operation of at least some of medical devices associated with the first medical signal processing device in accordance with an instruction from the user through a predetermined network.

(5)

The medical observation system according to (4), further comprising, as one of the medical devices, a device configured to provide predetermined treatment to the affected part.

(6)

The medical observation system according to (4), further comprising, as one of the medical devices, an instruction device supported to the medical observation device and configured to present an index to at least part of the affected part.

(7)

The medical observation system according to any one of (1) to (6), wherein
- the first medical signal processing device includes a first output control unit configured to control a first output unit to output a first image corresponding to a result of the first signal processing on the first image data, and
- the second medical signal processing device includes a second output control unit configured to control a second output unit to output a second image corresponding to a result of the second signal processing on the second image data.

(8)

The medical observation system according to (7), wherein the first output control unit and the second output control unit each control the corresponding output unit to output display information common to the first output control unit and the second output control unit.

(9)

The medical observation system according to (8), wherein the first output control unit and the second output control unit each control the corresponding output unit to output information related to a surgical procedure as the common display information.

(10)

The medical observation system according to (8) or (9), wherein
- the second output control unit updates the display information based on an instruction from a user associated with the second medical signal processing device, and
- the first output control unit reflects a result of the update on the display information displayed by the first output unit.

(11)

The medical observation system according to any one of (7) to (10), wherein
- the first signal processing unit
  - provides third signal processing to first information corresponding to a sensing result obtained by a predetermined sensing unit and including at least vital information of a patient,
  - transmits the first information provided with the third signal processing to the second medical signal processing device as second information, and
  - provides fourth signal processing to the first information provided with the third signal processing,
- the first output control unit controls the first output unit to output the first information provided with the fourth signal processing,
- the second signal processing unit provides fifth signal processing to the second information, and
- the second output control unit controls the second output unit to output the second information provided with the fifth signal processing.

(12)

The medical observation system according to (11), wherein the first signal processing unit controls the third signal processing based on an instruction from a user associated with the first medical signal processing device.

(13)

The medical observation system according to any one of (1) to (12), wherein the second signal processing unit controls the second signal processing in accordance with information related to a user associated with the second medical signal processing device.

(14)

The medical observation system according to (13), wherein the second signal processing unit performs, as the second signal processing, processing of changing a display aspect of the second image data in accordance with the information related to the user associated with the second medical signal processing device.

(15)

The medical observation system according to (14), wherein the second signal processing unit controls, as the second signal processing, at least one of processing related to color replacement, processing of increasing luminance, processing of increasing color difference, and processing of emphasizing a minute part of the affected part.

(16)

The medical observation system according to any one of (1) to (15), further comprising the medical observation device.

(17)

The medical observation system according to (16), wherein the medical observation device
- includes an endoscope unit including a lens barrel inserted into the body cavity of a patient, and
- captures an image of the affected part acquired by the endoscope unit.

(18)

The medical observation system according to (16), wherein the medical observation device
- includes a microscope unit configured to acquire an enlarged image of the affected part, and
- captures the enlarged image acquired by the microscope unit.

(19)

A medical signal processing device comprising a signal processing unit configured to provide first signal processing to first image data corresponding to a result of image capturing of an affected part by a medical observation device, wherein the signal processing unit controls the first signal processing in accordance with second signal processing provided to second image data corresponding to the result of image capturing at another device.

(20)

A medical signal processing device comprising a signal processing unit configured to acquire second image data corresponding to a result of image capturing of an affected part by a medical observation device from another device and provide second signal processing to the second image data, wherein the signal processing unit transmits information related to the second signal processing to the other device configured to control first signal processing on first image data corresponding to the result of image capturing.

(21)

A medical signal processing device driving method including, by a computer:
providing first signal processing to first image data corresponding to a result of image capturing of an affected part by a medical observation device,
in which the first signal processing is controlled in accordance with second signal processing provided to second image data corresponding to the result of image capturing at another device.

(22)

A medical signal processing device driving method including, by a computer:
acquiring second image data corresponding to a result of image capturing of an affected part by a medical observation device from another device and providing second signal processing to the second image data; and
transmitting information related to the second signal processing to the other device configured to control first signal processing on first image data corresponding to the result of image capturing.

(23)

A computer program configured to cause a computer to execute
providing first signal processing to first image data corresponding to a result of image capturing of an affected part by a medical observation device,
in which the first signal processing is controlled in accordance with second signal processing provided to second image data corresponding to the result of image capturing at another device.

(24)

A computer program configured to cause a computer to execute:
acquiring second image data corresponding to a result of image capturing of an affected part by a medical observation device from another device and providing second signal processing to the second image data; and
transmitting information related to the second signal processing to the other device configured to control first signal processing on first image data corresponding to the result of image capturing.

(25)

A medical observation system comprising:
a medical observation device; and
a medical signal processing device,
wherein the medical signal processing device includes
a first signal processing unit configured to provide signal processing to first image data corresponding to a result of image capturing of an affected part by the medical observation device to generate second image data,
a first output control unit configured to control a first output unit to output an image corresponding to the second image data, and
a forwarding processing unit configured to forward the first image data to another device.

(26)

The medical observation system according to (25), wherein the first signal processing unit provides, as first signal processing that is the signal processing, signal processing based on information in accordance with second signal processing provided to the first image data at another device.

(27)

The medical observation system according to (26), wherein information in accordance with the second signal processing is information different from the first image data provided with the second signal processing.

(28)

The medical observation system according to (26) or (27), wherein information in accordance with the second signal processing includes a parameter of the second signal processing.

(29)

The medical observation system according to any one of (26) to (28), further comprising a second medical signal processing device that is the other device and connected with a first medical signal processing device that is the medical signal processing device through a predetermined network, wherein
the second medical signal processing device includes
a second signal processing unit configured to provide the second signal processing to the first image data, and
a second output control unit configured to control a second output unit to output an image corresponding to a result of the second signal processing on the first image data, and
the second signal processing unit transmits information in accordance with the second signal processing to the first medical signal processing device.

(30)

The medical observation system according to (29), wherein
the forwarding processing unit sequentially forwards the first image data to the second medical signal processing device in accordance with a result of image capturing by the medical observation device,
the second signal processing unit provides the second signal processing to the sequentially acquired first image data, and
the second output control unit controls the second output unit to sequentially output an image corresponding to a result of the second signal processing on the first image data.

(31)

The medical observation system according to any one of (26) to (30), wherein the first signal processing includes processing related to image quality control.

(32)

The medical observation system according to any one of (26) to (30), wherein the first image data is RAW data corresponding to a result of image capturing by the medical observation device.

(33)

The medical observation system according to any one of (26) to (31), wherein the first image data is image data obtained by providing third signal processing different from the first signal processing to RAW data corresponding to a result of image capturing by the medical observation device.

(34)

The medical observation system according to any one of (25) to (33), wherein the medical observation device
includes an endoscope unit including a lens barrel inserted into the body cavity of a patient, and
captures an image of the affected part acquired by the endoscope unit.

(35)

The medical observation system according to any one of (25) to (33), wherein the medical observation device
includes a microscope unit configured to acquire an enlarged image of the affected part, and
captures the enlarged image acquired by the microscope unit.

(36)

A medical signal processing device comprising:
a signal processing unit configured to provide signal processing to first image data corresponding to a result of image capturing of an affected part by a medical observation device to generate second image data;
an output control unit configured to control an output unit to output an image corresponding to the second image data; and
a forwarding processing unit configured to forward the first image data to another device.

(37)

A medical signal processing device driving method comprising, by a computer:
providing signal processing to first image data corresponding to a result of image capturing of an affected part by a medical observation device to generate second image data;
controlling an output unit to output an image corresponding to the second image data; and
forwarding the first image data to another device.

REFERENCE SIGNS LIST 1 medical observation system
200 first system
201 image capturing device
202 input device
203 sound collection device
204 output device
211 detection device
213 medical device
230 information processing device
231 forwarding processing unit
232 signal processing unit
233 input-output control unit
234 device control unit
239 communication unit
300 second system
310 information processing device
311 signal processing unit
313 input-output control unit
315 device control unit
315 remote control unit
319 communication unit
320 input device
330 output device

The invention claimed is:

1. A medical observation system, comprising:
a first medical signal processing device including a first central processing unit (CPU), wherein the first CPU is configured to:
acquire first image data corresponding to a result of image capturing of an affected part by a medical observation device; and
provide first signal processing to the first image data; and
a second medical signal processing device including a second CPU, wherein the second CPU is configured to:
acquire second image data corresponding to the result of image capturing, from the first medical signal processing device through a specific network;
acquire specific information from a user associated with the second medical signal processing device, wherein the specific information is related to second signal processing;
provide the second signal processing to the second image data based on the specific information; and
transmit the specific information related to the second signal processing to the first medical signal processing device, wherein
the first CPU is further configured to:
control the first signal processing based on the second signal processing;
receive, from the second medical signal processing device through the specific network, a first instruction from the user associated with the second medical signal processing device; and
control, based on the received first instruction, an operation of at least one medical device associated with the first medical signal processing device.

2. The medical observation system according to claim 1, wherein
the second CPU is further configured to acquire the specific information through an input unit in a first room, and
the medical observation device is in a second room different from the first room.

3. The medical observation system according to claim 1, further comprising the at least one medical device configured to provide a specific treatment to the affected part.

4. The medical observation system according to claim 1, further comprising the at least one medical device supported to the medical observation device,
wherein the at least one medical device is configured to present an index to at least a part of the affected part.

5. The medical observation system according to claim 1, wherein
the first CPU is further configured to control a first display device to output a first image corresponding to a result of the first signal processing on the first image data, and
the second CPU is further configured to control a second display device to output a second image corresponding to a result of the second signal processing on the second image data.

6. The medical observation system according to claim 5, wherein the first CPU and the second CPU are further configured to control the first display device and the second display device, respectively, to output display information common to the first CPU and the second CPU.

7. The medical observation system according to claim 6, wherein the first CPU and the second CPU are further configured to control the first display device and the second display device, respectively, to output the display information related to a surgical procedure.

8. The medical observation system according to claim 6, wherein
the second CPU is further configured to update the display information based on the first instruction from the user associated with the second medical signal processing device, and
the first CPU is further configured to reflect a result of the update on the display information displayed by the first display device.

9. The medical observation system according to claim 5, wherein
the first CPU is further configured to:
provide third signal processing to first information corresponding to a sensing result by a sensor, wherein the first information includes vital information of a patient;
transmit the first information provided with the third signal processing to the second medical signal processing device as second information;
provide fourth signal processing to the first information provided with the third signal processing; and
control the first display device to output the first information provided with the fourth signal processing, and the second CPU is further configured to:
provide fifth signal processing to the second information; and
control unit control the second display device to output the second information provided with the fifth signal processing.

10. The medical observation system according to claim 9, wherein the first CPU is further configured to:
acquire a second instruction from a user associated with the first medical signal processing device; and
control the third signal processing based on the acquired second instruction.

11. The medical observation system according to claim 1, wherein the second CPU is further configured to control the second signal processing based on user information related to the user associated with the second medical signal processing device.

12. The medical observation system according to claim 11, wherein the second CPU is further configured to control, as the second signal processing, processing of changing a display aspect of the second image data based on the user information related to the user associated with the second medical signal processing device.

13. The medical observation system according to claim 12, wherein the second CPU is further configured to control, as the second signal processing, at least one of processing related to color replacement, processing of increasing luminance, processing of increasing color difference, or processing of emphasizing a minute part of the affected part.

14. The medical observation system according to claim 1, further comprising the medical observation device.

15. The medical observation system according to claim 14, wherein
the medical observation device includes an endoscope unit including a lens barrel insertable into a body cavity of a patient, and
the endoscope unit is configured to capture an image of the affected part.

16. The medical observation system according to claim 14, wherein
the medical observation device includes a microscope unit configured to acquire an enlarged image of the affected part, and
the medical observation device is configured to capture the enlarged image acquired by the microscope unit.

17. A first medical signal processing device, comprising:
a central processing unit (CPU) configured to:
acquire first image data corresponding to a result of image capturing of an affected part by a medical observation device;
provide first signal processing to the first image data;
control the first signal processing based on second signal processing provided to second image data by a second medical signal processing device,
wherein the second image data corresponds to the result of image capturing;
receive, from the second medical signal processing device through a specific network, an instruction from a user associated with the second medical signal processing device; and
control, based on the received instruction, an operation of at least one medical device associated with the first medical signal processing device.

18. A second medical signal processing device, comprising:
a second central processing unit (CPU) configured to:
acquire second image data corresponding to a result of image capturing of an affected part by a medical observation device, from a first medical signal processing device;
acquire an instruction and specific information from a user associated with the second medical signal processing device, wherein the specific information is related to second signal processing;
provide the second signal processing to the second image data based on the specific information;
transmit the instruction to the first medical signal processing device; and
transmit the specific information related to the second signal processing to the first medical signal processing device, wherein
the first medical signal processing device includes a first CPU that:
controls first signal processing based on the second signal processing,
receives, from the second medical signal processing device through a specific network, the instruction from the user associated with the second medical signal processing device, and
controls, based on the received instruction, an operation of at least one medical device associated with the first medical signal processing device.

19. A medical observation system, comprising:
a medical observation device; and
a first medical signal processing device, wherein
the first medical signal processing device includes a first central processing unit (CPU), wherein the first CPU is configured to:
provide first signal processing to first image data to generate second image data,
wherein the first image data corresponds to a result of image capturing of an affected part by the medical observation device;
control a first display device to output a first image corresponding to the second image data;
transmit the first image data to a second medical signal processing device;
control the first signal processing based on second signal processing of the second image data by the second medical signal processing device;
receive, from the second medical signal processing device through a specific network, an instruction from a user associated with the second medical signal processing device; and
control, based on the received instruction, an operation of at least one medical device associated with the first medical signal processing device.

20. The medical observation system according to claim 19, wherein
the first CPU is further configured to:
acquire specific information related to the second signal processing provided to the first image data, from the second medical signal processing device; and
provide the first signal processing based on the specific information.

21. The medical observation system according to claim 20, wherein the specific information is different from the first image data provided with the second signal processing.

22. The medical observation system according to claim 20, wherein the specific information includes a parameter of the second signal processing.

23. The medical observation system according to claim 20, further comprising the second medical signal processing device connected with the first medical signal processing device through the specific network, wherein
the second medical signal processing device includes a second CPU, and
the second CPU is configured to:
provide the second signal processing to the first image data;
control a second display device to output a second image corresponding to a result of the second signal processing on the first image data; and
transmit the specific information based on the second signal processing to the first medical signal processing device.

24. The medical observation system according to claim 23, wherein
the first CPU is further configured to sequentially transmit the first image data to the second medical signal processing device based on the result of image capturing by the medical observation device, and
the second CPU is further configured to:
sequentially acquire the first image data from the first medical signal processing device;
provide the second signal processing to the sequentially acquired first image data; and
control the second display device to sequentially output the second image corresponding to the result of the second signal processing on the first image data.

25. The medical observation system according to claim 20, wherein the first signal processing includes processing related to image quality control.

26. The medical observation system according to claim 20, wherein the first image data is raw data corresponding to the result of image capturing by the medical observation device.

27. The medical observation system according to claim 20, wherein
the first CPU is further configured to provide third signal processing to raw data corresponding to the result of image capturing by the medical observation device, to obtain the first image data, and
the third signal processing is different from the first signal processing.

28. The medical observation system according to claim 19, wherein
the medical observation device includes an endoscope unit including a lens barrel insertable into a body cavity of a patient, and
the endoscope unit is configured to capture an image of the affected part.

29. The medical observation system according to claim 19, wherein
the medical observation device includes a microscope unit configured to acquire an enlarged image of the affected part, and
the medical observation device is configured to capture the enlarged image acquired by the microscope unit.

30. A first medical signal processing device, comprising:
a central processing unit (CPU) configured to:
provide first signal processing to first image data to generate second image data,
wherein the first image data corresponds to a result of image capturing of an affected part by a medical observation device;
control a display device to output an image corresponding to the second image data;
transmit the first image data to a second medical signal processing device;
control the first signal processing based on second signal processing of the second image data by the second medical signal processing device;
receive, from the second medical signal processing device through a specific network, an instruction from a user associated with the second medical signal processing device; and
control, based on the received instruction, an operation of at least one medical device associated with the first medical signal processing device.

31. A method of driving a first medical signal processing device, the method comprising:
providing first signal processing to first image data to generate second image data,
wherein the first image data corresponds to a result of image capturing of an affected part by a medical observation device;
controlling a display device to output an image corresponding to the second image data;
transmitting the first image data to a second medical signal processing device;
controlling the first signal processing based on second signal processing of the second image data by the second medical signal processing device;
receiving, from the second medical signal processing device through a specific network, an instruction from a user associated with the second medical signal processing device; and
controlling, based on the received instruction, an operation of at least one medical device associated with the first medical signal processing device.

* * * * *